United States Patent
Ullah et al.

(10) Patent No.: US 10,633,316 B2
(45) Date of Patent: Apr. 28, 2020

(54) METHODS FOR CONVERTING GLYCEROL TO ALLYL COMPOUNDS

(71) Applicant: The Governors of the University of Alberta, Edmonton (CA)

(72) Inventors: Aman Ullah, Edmonton (CA); Yanet Rodriguez Herrero, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 0 days.

(21) Appl. No.: 16/454,954

(22) Filed: Jun. 27, 2019

(65) Prior Publication Data

US 2020/0002256 A1     Jan. 2, 2020

Related U.S. Application Data

(60) Provisional application No. 62/691,308, filed on Jun. 28, 2018.

(51) Int. Cl.
| | |
|---|---|
| *C07C 29/60* | (2006.01) |
| *C07C 45/71* | (2006.01) |
| *C07C 47/21* | (2006.01) |
| *C07C 33/025* | (2006.01) |
| *C08F 16/08* | (2006.01) |
| *C08G 6/00* | (2006.01) |

(52) U.S. Cl.
CPC .............. *C07C 29/60* (2013.01); *C07C 45/71* (2013.01); *C08F 16/08* (2013.01); *C08G 6/00* (2013.01); *C07C 33/025* (2013.01); *C07C 47/21* (2013.01)

(58) Field of Classification Search
CPC ....... C07C 29/60; C07C 45/71; C07C 33/025; C07C 47/21; C08G 6/00; C08F 16/08
See application file for complete search history.

(56) References Cited

U.S. PATENT DOCUMENTS

| | | | | |
|---|---|---|---|---|
| 3,285,897 A | * | 11/1966 | Sullivan | ........... C08F 16/00 526/196 |
| 9,120,718 B1 | * | 9/2015 | Kim | ........... C07C 29/147 |
| 2009/0287004 A1 | * | 11/2009 | Bergman | ........... C07C 29/60 549/508 |

FOREIGN PATENT DOCUMENTS

BR          8904178    *   2/1991

* cited by examiner

*Primary Examiner* — Paul A Zucker
(74) *Attorney, Agent, or Firm* — Clark & Elbing LLP

(57) ABSTRACT

The present disclosure is directed towards methods of converting glycerol to an allyl compound, involving deoxydehydrating glycerol with formic acid and heat to form allyl alcohol; and esterifying the allyl alcohol with formic acid and/or phthalic anhydride and heat to form allyl formate and diallyl phthalate. In some instances, the heat is generated by a microwave. In further instances, the methods involve polymerizing the allyl alcohol, allyl formate and/or diallyl phthalate to form poly(allyl alcohol) or poly(allyl formate) or poly (diallyl phthalate). In some instances, the allyl polymers were used for the consolidation of oil sands tailings.

19 Claims, 24 Drawing Sheets

II

III

I

II

METHODS FOR CONVERTING GLYCEROL TO ALLYL COMPOUNDS

CROSS REFERENCE TO RELATED APPLICATION

This application claims priority to U.S. provisional patent application U.S. 62/691,308, filed Jun. 28, 2018, the entire contents of which is hereby incorporated by reference.

FIELD

The present disclosure relates generally to conversions of oleo-chemical byproducts. More particularly, the present disclosure relates to methods for converting glycerol to allyl compounds.

BACKGROUND

About 10-11% (w/w) glycerol is generated as a main by-product of the biodiesel and oleochemical industries. It is estimated that the world biodiesel market will reach 37 billion gallons by 2016 [Yang F, Hanna M A, Sun R. Biotechnology for Biofuels, 2012. 5(1): p. 13], leading to approximately 4 billion gallons of crude glycerol production [Hiremath A, Kannabiran M, Rangaswamy V. New Biotechnology, 2011. 28(1): p. 19-23]. According to estimates, about 2.8 million tonnes of crude glycerol is also produced in Alberta annually. This crude glycerol is expensive to purify and becomes economically unviable to be used in food, pharmaceutical, or cosmetics industries, where pure glycerol is needed. In recent years, with a rapid expansion in biodiesel production, the biodiesel industry is facing a dilemma of how to meet an ever-growing biofuel demand, and manage excessive crude glycerol so that it does not pose a threat to the environment. Therefore, several approaches to utilize/dispose crude glycerol have been investigated, including compositing [Sadano Y, Toshimitsu R, Kohda J, Nakano Y, Yano T. Journal of Material Cycles and Waste Management, 2010. 12(4): p. 308-313], animal feed [Nitayavardhana S, Khanal S K. Bioresource Technology, 2011. 102(10): p. 5808-5814], combustion [Coronado C R, Carvalho J A, Quispe C A, Sotomonte C R. 63(1): p. 97-104], thermochemical [Luo X, Hu S, Zhang X, Li Y. Bioresource Technology, 2013. 139: p. 323-329; Maglinao R L, He B B. Industrial & Engineering Chemistry Research, 2011. 50(10): p. 6028-6033], and biological/microbial conversions [Yazdani S S, Gonzalez R. Current Opinion in Biotechnology, 2007. 18(3): p. 213-219; Xu J, Zhao X, Wang W, Du W, Liu D. Biochemical Engineering Journal, 2012. 65: p. 30-36]. Nevertheless, due to the high amount of impurities, direct utilization of the glycerol is not a viable option and a majority of current conversion approaches lead to either low conversion yields, high amount of co-products during conversion, and high energy consumption, which hampers the large scale viability of such processes. Therefore, the selective conversion of this bio-resource into high value products remains a challenge, and the development of new rapid, efficient and economically viable methodologies is desirable.

Therefore, the transformation of glycerol into valuable compounds has been investigated. Glycerol has been used in the production of hydrogen [Buffoni I N, Pompeo F, Santori G F, Nichio N N. Catalysis Communications, 2009. 10(13): p. 1656-1660; Sabourin-Provost G, Hallenbeck P C. Bioresource Technology, 2009. 100(14): p. 3513-3517], dihydroxyacetone [Painter R M, Pearson D M, Waymouth R M. Angewandte Chemie International Edition, 2010. 49(49): p. 9456-9459], propanediols [Gandarias I, Arias P, Requies J, Güemez M, Fierro J. Applied Catalysis B: Environmental, 2010. 97(1): p. 248-256; Guo L, Zhou J, Mao J, Guo X, Zhang S. Applied Catalysis A: General, 2009. 367(1): p. 93-98], acrolein [Ning L, Ding Y, Chen W, et al. Chinese Journal of Catalysis, 2008. 29(3): p. 212-214; Ulgen A, Hoelderich W F. Applied Catalysis A: General, 2011. 400 (1-2): p. 34-38; Alhanash A, Kozhevnikova E F, Kozhevnikov I V. Applied Catalysis A: General, 2010. 378(1): p. 11-18], glycerides [Xu J, Zhao X, Wang W, Du W, Liu D. Biochemical Engineering Journal, 2012. 65: p. 30-36], epichlorohydrin [Dibenedetto A, Angelini A, Aresta M, Ethiraj J, Fragale C, Nocito F. Tetrahedron, 2011. 67(6): p. 1308-1313; Santacesaria E, Tesser R, Di Serio M, Casale L, Verde D. Industrial & Engineering Chemistry Research, 2009. 49(3): p. 964-970.], allyl alcohol [Kamm O, Marvel C. Org. Syn, 1921. 1: p. 15-17; Arceo E, Marsden P, Bergman R G, Ellman J A. Chemical Communications, 2009. (23): p. 3357-3359], acrylic acid [Li X, Zhang Y. ACS Catalysis, 2016. 1(6): p. 143-150; Omata K, Matsumoto K, Murayama T, Ueda W. Catalysis Today, 2016. 259, Part 1: p. 205-212.; Liu L, Wang B, Du Y, Zhong Z, Borgna A. Applied Catalysis B: Environmental, 2015. 174-175: p. 1-12; Possato L G, Cassinelli W H, Garetto T, Pulcinelli S H, Santilli C V, Martins L. Applied Catalysis A: General, 2015. 492: p. 243-251; Shen L, Yin H, Wang A, Lu X, Zhang C. Chemical Engineering Journal, 2014. 244: p. 168-177], lactic acid [Yin H, Zhang C, Yin H, Gao D, Shen L, Wang A. Chemical Engineering Journal, 2016. 288: p. 332-343; Ftouni J, Villandier N, Auneau F, Besson M, Djakovitch L, Pinel C. Catalysis Today, 2015. 257, Part 2: p. 267-273], acrylonitrile [Calvino-Casilda V, Guerrero-Pérez M O, Banares M A. Applied Catalysis B: Environmental, 2010. 95(3-4): p. 192-196], and glycerol carbonate [Dibenedetto A, Angelini A, Aresta M, Ethiraj J, Fragale C, Nocito F. Tetrahedron, 2011. 67(6): p. 1308-1313]. The transformation of glycerol requires in general use of solid catalysts including heteropolyacids [Martinuzzi I, Azizi Y, Zahraa O, Leclerc J. Chemical Engineering Science, 2015. 134: p. 663-670; Martin A, Armbruster U, Atia H. European Journal of Lipid Science and Technology, 2012. 114(1): p. 10-23; Erfle S, Armbruster U, Bentrup U, Martin A, Bruckner A. Applied Catalysis A: General, 2011. 391(1-2): p. 102-109], metal oxides [Braga T P, Essayem N, Valentini A. RSC Advances, 2015. 5(113): p. 93394-93402; Chai S, Tao L, Yan B, Vedrine J C, Xu B. RSC Advances, 2014. 4(9): p. 4619-4630] and zeolites [Possato L G, Cassinelli W H, Garetto T, Pulcinelli S H, Santilli C V, Martins L. Applied Catalysis A: General, 2015. 492: p. 243-251; dos Santos M B, Andrade H M C, Mascarenhas A J S. Microporous and Mesoporous Materials, 2016. 223: p. 105-113; Näfe G, Lopez-Martinez M-, Dyballa M, et al. Journal of Catalysis, 2015. 329: p. 413-424; Carrico C S, Cruz F T, dos Santos M B, et al. Journal of Catalysis, 2016. 334: p. 34-41] at high temperature. Coke deposition [Cheng C K, Foo S Y, Adesina A A. Catalysis Today, 2011. 164(1): p. 268-274] is reported as a cause for catalyst deactivation and low selectivity and conversion. Allyl alcohol (AA) is an important building block for the production of glycidyl ethers [LIU H, ZHANG Z, ZOU J. Industrial Catalysis, 2003. 12: p. 006], esters [Mitsunobu O, Yamada M. Bulletin of the Chemical Society of Japan, 1967. 40(10): p. 2380-2382], amines [Kinoshita H, Shinokubo H, Oshima K. Organic Letters, 2004. 6(22): p. 4085-4088], poly (allyl alcohol) [Volodina V, Tarasov A, Spasskii S. Russian Chemical Reviews, 1970. 39(2): p. 140; Laible R. Chemical Reviews, 1958. 58(5): p. 807-843], and a variety of polymerizable esters like diallyl phthalate [Guo S. In: ACS Publications; 2000].

Canada has over 90% of the total known volumes of oil sands reserves[52] and the Athabasca oil sands deposit is the largest petroleum reserve in the world. Due to exhausting conventional oil resources, bitumen production from oil sands is gaining more attention for the production of synthetic crude oil from tar sands (bitumen). The increasing footprint of fluid fine tailings produced during bitumen extraction from oil sands ores is one of the major environmental concerns that Alberta is facing in the wake of oil sands development. In tailings ponds, coarse solids settle quickly as sand beach while fine particles settle at extremely slow rate. After an extended period of settling, a stable suspension containing about 30 wt % solids is formed that is known as Mature Fine Tailings (MFT). Further densification of dispersed clay particles in fine tailings could take decades, if not centuries, leading to continuous accumulation of MFT at alarming rate.

Various physical, chemical and biological means have been utilized and studied for effective consolidation to reclaim the MFT [X. Li, Y. Feng, J. J. Slaski, M. Fung, Journal of Canadian Petroleum Technology 2003, 42, 47-50; P. Mpofu, J. Addai-Mensah, J. Ralston, Minerals Engineering 2004, 17, 411-423; S. Proskin, D. Sego, M. Alostaz, Cold Regions Science and Technology 2010, 63, 110-120; A. Sworska, J. S. Laskowski, G. Cymerman, International Journal of Mineral Processing 2000, 60, 143-152; X. W. Wang, X. Feng, Z. Xu, J. H. Masliyah, Canadian Journal of Chemical Engineering 2010, 88, 403-410]. Nevertheless these technologies are unsuitable economically and environmentally. The use of gypsum by oil sand industries to enhance the rate of densification results in the constant build-up of calcium and sulfate ions in the recycled water impeding the effectiveness of bitumen extraction[E. Redfield, C. Croser, J. J. Zwiazek, M. D. MacKinnon, C. Qualizza, Journal of Environmental Quality 2003, 32, 1008-1014]. Anionic polymers (polyacrylamides and their derivatives) with high molecular weight have also been used commercially as an organic flocculants to treat fine tailings, providing an enhanced rate of consolidation. However, this require a high dosage of polymer which results in the detachment of clay particles instead of flocks to be settled because of their loose interaction in between clay particles and polymer[J. G. Matthews, W. H. Shaw, M. D. MacKinnon, R. G. Cuddy, International Journal of Surface Mining, Reclamation and Environment 2002, 16, 24-39]. In addition, the fate of these synthetic flocculants is not well known considering some initial reports on degradation of PAM to acrylamide monomer which is a known neurotoxin and potentially human carcinogen.

SUMMARY

In an aspect of the present disclosure, there is provided a method of converting glycerol to an allyl compound, comprising deoxydehydrating glycerol with formic acid and heat to form allyl alcohol; and esterifying the allyl alcohol with formic acid and heat to form allyl formate.

In an embodiment of the present disclosure, there is provided a method wherein the heat is generated by a microwave.

In another embodiment, there is provided a method wherein deoxydehydrating the glycerol with the formic acid and heat to form the allyl alcohol comprises heating the glycerol and the formic acid to about 195° C., and then heating the glycerol and the formic acid to about 260° C.

In another embodiment, there is provided a method further comprising isolating the allyl alcohol while heating the glycerol and the formic acid to about 260° C.

In another embodiment, there is provided a method further comprising cooling the glycerol and the formic acid to between about 95°-100° C., and then adding more of the formic acid.

In another embodiment, there is provided a method wherein heating the glycerol and the formic acid to about 195° C., then heating the glycerol and the formic acid to about 260° C., and cooling the glycerol and the formic acid to between about 95°-100° C., and then adding more of the formic acid is repeated three times.

In another embodiment, there is provided a method wherein esterifying the allyl alcohol with formic acid and heat to form allyl formate comprises heating the allyl alcohol and formic acid at about 60° C.

In another embodiment, there is provided a method, wherein the glycerol has a % purity of about 82-100%.

In another embodiment, there is provided a method wherein the allyl alcohol formed has a purity of 90%.

In another embodiment, there is provided a method wherein the allyl alcohol formed has a purity of about 95%.

In another embodiment, there is provided a method wherein the allyl formate formed has a purity of 85%.

In another embodiment, there is provided a method wherein the allyl formate formed has a purity of about 90%.

In another embodiment, there is provided a method further comprising polymerizing the allyl formate using a radical initiator and heat to form poly(allyl formate).

In another embodiment, there is provided a method wherein the heat is generated by a microwave.

In another embodiment, there is provided a method wherein the poly(allyl formate) has a molecular weight of at least 1000 g/mol.

In another embodiment, there is provided a method wherein the poly(allyl formate) has a molecular weight of at least 1150 g/mol.

In another embodiment, there is provided a method wherein the radical initiator is α,α'-azoisobutyronitrile, tert-butyl perbenzoate, di-tert-butyl peroxide, tert-butyl hyperoxide, or benzoyl peroxide.

In another aspect of the present disclosure, there is provided a use of the allyl formate formed from the method as described herein as a solvent in spray lacquers, enamels, varnishes, or latex paints.

In another aspect, there is provided a use of the allyl formate formed from the method as described herein as an ingredient in paint thinners, paint strippers, varnish removers, or herbicides.

In another aspect, there is provided a use of the allyl formate formed from the method as described herein as a co-monomer with maleic anhydride, vinyl stearate, and vinyl triethoxysilane to prepare protective coatings for glass.

In another aspect of the present disclosure, there is provided a use of the poly(allyl formate) formed from the method as described herein as a reactive plasticizer. In an embodiment, the poly(allyl formate) is used as reactive plasticizer in thermoplastics processing.

In another aspect of the present disclosure, there is provided a method of converting glycerol to an allyl compound, comprising deoxydehydrating glycerol with formic acid by microwave-assisted distillation to form allyl alcohol; and esterifying the allyl alcohol with formic acid by microwave-assisted reflux to form allyl formate.

In another embodiment of the present disclosure, there is provided a method wherein deoxydehydrating the glycerol with the formic acid by microwave-assisted distillation to form the allyl alcohol comprises distilling the glycerol and the formic acid at about 195° C., and then distilling the glycerol and the formic acid up to about 260° C.

In another embodiment, there is provided a method further comprising isolating the allyl alcohol while distilling the glycerol and the formic acid up to about 260° C.

In another embodiment, there is provided a method further comprising cooling the glycerol and the formic acid to between about 95°-100° C., and then adding more of the formic acid.

In another embodiment, there is provided a method wherein distilling the glycerol and the formic acid at about 195° C., then distilling the glycerol and the formic acid up to about 260° C., and cooling the glycerol and the formic acid to between about 95°-100° C., and then adding more of the formic acid is repeated three times.

In another embodiment, there is provided a method wherein esterifying the allyl alcohol with formic acid by microwave-assisted reflux to form allyl formate comprises distilling the allyl alcohol and formic acid at about 60° C.

In another embodiment, there is provided a method wherein the glycerol has a % purity of about 82-100%.

In another embodiment, there is provided a method wherein the allyl alcohol formed has a purity of 90%.

In another embodiment, there is provided a method wherein the allyl alcohol formed has a purity of about 95%.

In another embodiment, there is provided a method wherein the allyl formate formed has a purity of 85%.

In another embodiment, there is provided a method wherein the allyl formate formed has a purity of about 90%.

In another embodiment, there is provided a method further comprising polymerizing the allyl formate using a radical initiator and microwave-assisted heating to form poly(allyl formate).

In another embodiment, there is provided a method wherein the poly(allyl formate) has a molecular weight of at least 1000 g/mol.

In another embodiment, there is provided a method wherein the poly(allyl formate) has a molecular weight of at least 1150 g/mol.

In another embodiment, there is provided a method wherein the radical initiator is α,α'-azoisobutyronitrile, tert-butyl perbenzoate, di-tert-butyl peroxide, tert-butyl hydroperoxide, or benzoyl peroxide.

In another aspect of the present disclosure, there is provided a use of the allyl formate formed from the method as described herein as a solvent in spray lacquers, enamels, varnishes, or latex paints.

In another aspect, there is provided a use of the allyl formate formed from the method as described herein as a co-monomer with maleic anhydride, vinyl stearate, and vinyl triethoxysilane to prepare protective coatings for glass.

In another aspect, there is provided a use of the allyl formate formed from the method as described herein as an ingredient in paint thinners, paint strippers, varnish removers, or herbicides.

In another aspect of the present disclosure, there is provided a use of the poly(allyl formate) formed from the method as described herein as a reactive plasticizer. In an embodiment, the poly(allyl formate) is used as reactive plasticizer in thermoplastics processing.

In another aspect of the present disclosure, there is provided a method of converting glycerol to an allyl polymer, comprising deoxydehydrating glycerol with formic acid and heat to form allyl alcohol; and polymerizing the allyl alcohol using a radical initiator and heat to form poly(allyl alcohol).

In another embodiment of the present disclosure, there is provided a method wherein, wherein the heat is generated by a microwave.

In another embodiment, there is provided a method wherein deoxydehydrating the glycerol with the formic acid and heat to form the allyl alcohol comprises heating the glycerol and the formic acid to about 195° C., and then heating the glycerol and the formic acid to about 260° C.

In another embodiment, there is provided a method further comprising isolating the allyl alcohol while heating the glycerol and the formic acid to about 260° C.

In another embodiment, there is provided a method further comprising cooling the glycerol and the formic acid to between about 95°-100° C., and then adding more of the formic acid.

In another embodiment, there is provided a method wherein heating the glycerol and the formic acid to about 195° C., then heating the glycerol and the formic acid to about 240° C., and cooling the glycerol and formic acid to between about 95°-100° C., and then adding more of the formic acid is repeated three times.

In another embodiment, there is provided a method wherein the glycerol has a % purity of about 82-100%.

In another embodiment, there is provided a method wherein the allyl alcohol formed has a purity of 90%.

In another embodiment, there is provided a method wherein the allyl alcohol formed has a purity of about 95%.

In another embodiment, there is provided a method wherein the poly(allyl alcohol) has a molecular weight of at least 2400 g/mol.

In another embodiment, there is provided a method wherein the poly(allyl alcohol) has a molecular weight of at least 2530 g/mol.

In one aspect there is described a method of converting glycerol to an allyl compound, comprising: (a) deoxydehydrating glycerol with formic acid and heat to form allyl alcohol; and (b) esterifying the allyl alcohol with formic acid and heat to form allyl formate.

In one example, the heat is generated by a microwave.

In one example, microwave assists: (a) deoxydehydrating glycerol with formic acid and heat by distillation to form allyl alcohol; and (b) esterifying the allyl alcohol with formic acid and heat by reflux to form allyl formate.

In one example, deoxydehydrating the glycerol with the formic acid and heat to form the allyl alcohol comprises heating the glycerol and the formic acid to about 195° C., and then heating the glycerol and the formic acid to about 240° C.

In one example, further comprising isolating the allyl alcohol while heating the glycerol and the formic acid to about 240° C.

In one example, further comprising cooling the glycerol and the formic acid to between about 95°-100° C., and then adding more of the formic acid.

In one example, wherein esterifying the allyl alcohol with formic acid and heat to form allyl formate comprises heating the allyl alcohol and formic acid at about 60° C.

In one example, wherein the allyl alcohol formed has a purity of 90%.

In one example, wherein the allyl formate formed has a purity of 85%.

In one example, further comprising polymerizing the allyl formate using α,α'-azoisobutyronitrile, tert-butyl perbenzoate, di-tert-butyl peroxide, tert-butyl hydroperoxide, or benzoyl peroxide and heat to form poly(allyl formate).

In one example, wherein the poly(allyl formate) has a molecular weight of at least 1000 g/mol.

In one aspect there is provided a method of converting glycerol to an allyl polymer, comprising: (a) deoxydehydrating glycerol with formic acid and heat to form allyl alcohol; and (b) polymerizing the allyl alcohol using a radical initiator and heat to form poly(allyl alcohol).

In one example, wherein the heat is generated by a microwave.

In one example, wherein a microwave assists: (a) deoxydehydrating glycerol with formic acid and heat by distillation to form allyl alcohol; and (b) polymerizing the allyl alcohol using a radical initiator and heat by reflux to form poly(allyl alcohol).

In one example, wherein deoxydehydrating the glycerol with the formic acid and heat to form the allyl alcohol comprises heating the glycerol and the formic acid to about 195° C., and then heating the glycerol and the formic acid to about 260° C.

In one example, further comprising isolating the allyl alcohol while heating the glycerol and the formic acid to about 260° C.

In one example, further comprising cooling the glycerol and the formic acid to between about 95°-100° C., and then adding more of the formic acid.

In one example, wherein the allyl alcohol formed has a purity of 90%.

In one example, wherein the allyl alcohol formed has a purity of about 95%.

In one example, wherein the poly(allyl alcohol) has a molecular weight of at least 2400 g/mol.

BRIEF DESCRIPTION OF THE FIGURES

Embodiments of the present disclosure will now be described, by way of example only, with reference to the attached Figures.

DETAILED DESCRIPTION

Figure 1:
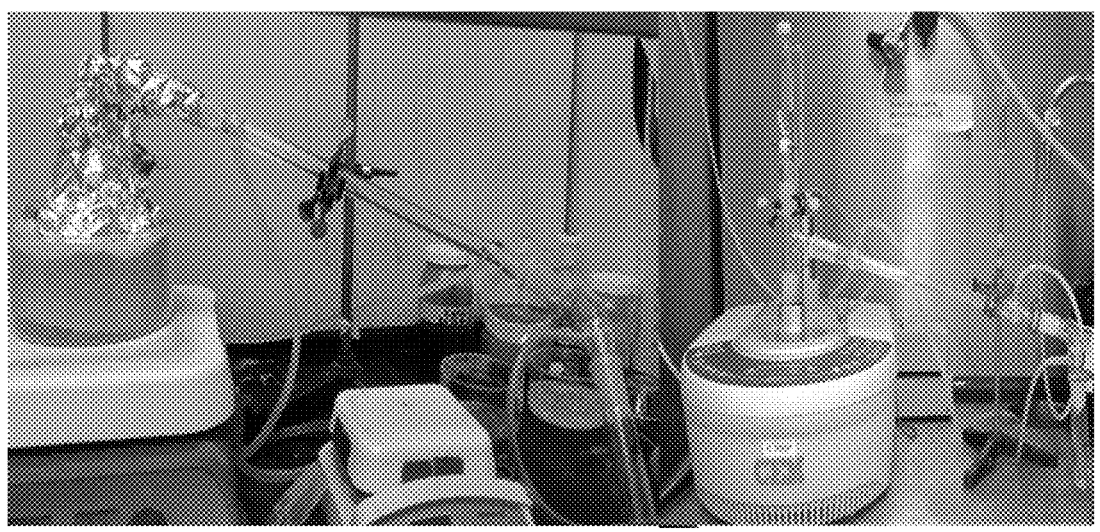
FIG. 1 depicts a sand bath (left) and microwave CEM Discovery (right) setup for preparation and purification of AA, wherein a round bottom flask was connected to a two-way adapter to connect a condenser and a receiving flask; temperature in the reaction mixture was measured by an immersed thermometer; flask was placed in a sand bath and covered with aluminum foil paper to preserve the heat; the round bottom flask was connected to a three-way adapter connected to addition funnel and a condenser; and, the condenser was connected to a vacuum adapter to connect the receiving flask.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

The term "deoxydehydration" or "deoxydehydrating" as used herein refers to a chemical reaction wherein two adjacent hydroxyl groups in a compound are removed to form an alkene.

The term "esterification" or "esterifying" as used herein refers to a chemical reaction between a carboxylic acid and an alcohol to form an ester.

As used herein, "glycerol" refers to a compound having the chemical formula $HOCH_2CH(OH)CH_2OH$. In an example, as described herein, the term "glycerol" also refers to substituted glycerols.

As used herein, "allyl alcohol" refers to a compound having the chemical formula $CH_2CHCH_2OH$, and the structural formula $CH_2=CHCH_2OH$.

As used herein, "allyl formate" refers to a compound having the chemical formula $CH_2CHCH_2OC(O)H$, and the structural formula $CH_2=CHCH_2OC(O)H$.

As used herein, "microwave-assisted distillation" or "microwave-assisted reflux" or "microwave-assisted heating" refers to a distillation or reflux or heating wherein a microwave is used as a heat source. Further, as used herein, "reflux" refers to a distillation involving the condensation of vapours, and the return of the condensed vapours to the system from which it was distilled.

As used herein, the term "polymer" means a molecule of high relative molecular mass, the structure of which essentially comprises multiple repetitions of units derived from molecules of low relative molecular mass. The term "oligomer" refers to a molecule of intermediate relative molecular mass, the structure of which essentially comprises a small plurality of units derived from molecules of low relative molecular mass. A molecule can be regarded as having a high relative molecular mass if the addition or removal of one or a few of the units has a negligible effect on the molecular properties. A molecule can be regarded as having an intermediate relative molecular mass if it has molecular properties which do vary significantly with the removal of one or a few of the units. (See IUPAC Recommendations 1996 in (1996) Pure and Applied Chemistry 68: 2287-2311.). Thus, as used herein, the term "poly(allyl alcohol)" refers to a polymer or oligomer comprising repetitions of units derived from allyl alcohol. Further, as used herein, the term "poly(allyl formate)" refers to a polymer or oligomer comprising repetitions of units derived from allyl formate.

In an aspect of the present disclosure, there is provided methods for converting glycerol to allyl compounds. In an example, there is a method of converting glycerol to an allyl compound, comprising deoxydehydrating glycerol with formic acid and heat to form allyl alcohol; and esterifying the allyl alcohol with formic acid and heat to form allyl formate. In another example, there is a method of converting glycerol to an allyl polymer, comprising deoxydehydrating glycerol with formic acid and heat to form allyl alcohol; and polymerizing the allyl alcohol using a radical initiator and heat to form poly(allyl alcohol). In some examples, there is a method wherein the heat is generated by a microwave. In another example, there is a method of converting glycerol to an allyl compound, comprising deoxydehydrating glycerol with formic acid by microwave-assisted distillation to form allyl alcohol; and esterifying the allyl alcohol with formic acid by microwave-assisted reflux to form allyl formate.

Microwave-assisted heating, or microwave (MW) efficiency is based on a heating of materials by microwave dielectric heating effects. This phenomenon is considered dependent on an ability of a specific material (e.g., catalyst, solvent, or reagent) to adsorb microwave energy and convert it into heat. A key parameter is considered a 'loss factor' or 'loss tangent' (tan $\delta$), which is a quotient between a dielectric loss ($\varepsilon''$) accounting for efficiency in converting electromagnetic radiation into heat, and a dielectric constant ($\varepsilon'$) that describes molecular polarization by an electric field. High tan $\delta$ values are indicative of high microwave absorption and rapid heating. It is considered that the resultant rapid and efficient conversions might be due to change in activation energy and pre-exponential factor of polar species under microwave irradiation.

In examples of the method described herein, there is an observed increased rate of converting glycerol to an allyl compound when using microwave-assisted heating relative to conventional heating methods, such as heating with a heating mantel and sand bath. In other examples of the method described herein, the rate of converting glycerol to an allyl compound requires less than one hour to reach completion when using microwave-assisted heating, relative to several hours to reach completion when using conventional heating methods.

In other examples, there is a method wherein deoxydehydrating the glycerol with the formic acid and heat to form the allyl alcohol comprises heating the glycerol and the formic acid to about 195° C., and then heating the glycerol and the formic acid to about 240° C.

In other examples, there is a method further comprising isolating the allyl alcohol while heating the glycerol and the formic acid to about 240° C.

In other examples, there is a method further comprising cooling the glycerol and the formic acid to between about 95°-100° C., and then adding more of the formic acid.

In other examples, there is a method wherein heating the glycerol and the formic acid to about 195° C., then heating the glycerol and the formic acid to about 240° C., and cooling the glycerol and the formic acid to between about 95°-100° C., and then adding more of the formic acid is repeated three times.

In other examples, there is a method esterifying the allyl alcohol with formic acid and heat to form allyl formate comprises heating the allyl alcohol and formic acid at about 60° C.

In other examples, there is a method wherein the glycerol has a % purity of about 82-100%. In other examples, there is a method wherein the allyl alcohol formed has a purity of 90%, or about 95%. In other examples, there is a method wherein the allyl formate formed has a purity of 85%, or about 90%.

In other examples, there is a method further comprising polymerizing the allyl formate using a radical initiator and heat to form poly(allyl formate). In some examples, the heat is generated by a microwave.

In other examples, there is a method wherein the poly (allyl formate) has a molecular weight of at least 1000 g/mol, or of at least 1150 g/mol.

In other examples, there is a method wherein the radical initiator is $\alpha,\alpha'$-azoisobutyronitrile, tert-butyl perbenzoate, di-tert-butyl peroxide, tert-butyl hydroperoxide, or benzoyl peroxide.

In yet other examples, there is a method wherein deoxydehydrating the glycerol with the formic acid by microwave-assisted distillation to form the allyl alcohol comprises distilling the glycerol and the formic acid at about 195° C., and then distilling the glycerol and the formic acid up to about 240° C.

In yet other examples, there is a method further comprising isolating the allyl alcohol while distilling the glycerol and the formic acid up to about 240° C.

In yet other examples, there is a method further comprising cooling the glycerol and the formic acid to between about 95°-100° C., and then adding more of the formic acid.

In yet other examples, there is a method wherein distilling the glycerol and the formic acid at about 195° C., then distilling the glycerol and the formic acid up to about 240° C., and cooling the glycerol and the formic acid to between about 95°-100° C., and then adding more of the formic acid is repeated three times.

In yet other examples, there is a method wherein esterifying the allyl alcohol with formic acid by microwave-assisted reflux to form allyl formate comprises distilling the allyl alcohol and formic acid at about 60° C.

In yet other examples, there is a method wherein the glycerol has a % purity of about 82-100%. In yet other examples, there is a method wherein the allyl alcohol formed has a purity of 90%, or of about 95%. In yet other examples, there is a method wherein the allyl formate formed has a purity of 85, or of about 90%.

In yet other examples, there is a method further comprising polymerizing the allyl formate using a radical initiator and microwave-assisted heating to form poly(allyl formate).

In yet other examples, there is a method wherein the poly(allyl formate) has a molecular weight of at least 1000 g/mol, or of at least 1150 g/mol.

In yet other examples, there is a method wherein the radical initiator is α,α'-azoisobutyronitrile, tert-butyl perbenzoate, di-tert-butyl peroxide, tert-butyl hydroperoxide, or benzoyl peroxide.

In yet another example, there is a method wherein the poly(allyl formate) has a molecular weight of at least 2400 g/mol, or of at least 2530 g/mol.

In some examples of the method described herein, the glycerol is optionally substituted.

In other examples, there is a method wherein the heat is generated from a conventional heating source, such as but not limited to a heating mantle and a sand bath. In some examples, wherein the heat is generated from a conventional heating source, deoxydehydrating the glycerol with the formic acid and heat to form the allyl alcohol comprises heating the glycerol and the formic acid to about 210° C. In some examples, wherein the heat is generated from a conventional heating source, esterifying the allyl alcohol with the formic acid and heat to form the allyl formate comprises heating the allyl alcohol and the formic acid to about 60° C.

In another example, there is a use of the allyl formate formed from the method as described herein as a solvent in spray lacquers, enamels, varnishes, or latex paints. In another example, there is a use of the allyl formate formed from the method as described herein as an ingredient in paint thinners, paint strippers, varnish removers, or herbicides. In another example, there is a use of the allyl formate formed from the method as described herein as a co-monomer with maleic anhydride, vinyl stearate, and vinyl triethoxysilane to prepare protective coatings for glass. In another example, there is a use of the poly(allyl formate) formed from the method as described herein as a reactive plasticizer. In some examples, the poly(allyl formate) is used as reactive plasticizer in thermoplastics processing.

The high reactivity of allyl alcohol makes it useful in the synthesis of pesticides, plastics, and intermediates. Allyl alcohol reacts with organic acids or acid anhydrides at moderate temperatures to produce esters. This high reactivity favors the synthesis of unsaturated polyesters with terminal allyl groups. Allyl alcohol reacts with unsaturated fatty acids to give drying oils. It can be copolymerized with styrene in the presence of oxygen for faster drying oils with excellent durability. It can be grafted to polyimides to improve heat and solvent resistance. The reaction of methyl glucoside polyethers with allyl alcohol, followed by bromination and addition of isocyanates, provides flame resistant polyurethane foams. Mono- or poly-functional allylic monomers also may be added as regulators or modifiers of vinyl polymerization for controlling molecular weight and polymer properties. The allyl resins have found extensive applications in electronic, electrical engineering, and biomaterials because of their physical and electrical properties. Further, co-polymerized allyl alcohol can be used as an intermediate in the production of flame-resistant materials that can be incorporated into plastics, resins, and fibers.

To gain a better understanding of the invention described herein, the following examples are set forth. It should be understood that these examples are for illustrative purposes only. Therefore, they should not limit the scope of this invention in anyway.

EXAMPLES

Example 1—Allyl Monomers and Polymers from Glycerol

As by-products of deoxydehydration (DODH) of glycerol, formic acid, water, carbon dioxide, and allyl formate (AF) are produced. AF being a minor by-product in the DODH process, previous research has focused on reducing or removing the AF, however it has been found, as described herein, that AF can be rapidly produced as a major product through easy esterification of AA with formic acid under microwave heating at low temperatures (60° C.), and can be easily separated from an aqueous solution. Generally, conversion of glycerol to AA has been carried out at high temperatures by using conventional heating over extended periods of time. Overall, microwave-assisted pyrolysis of glycerol to syngas, esterification of glycerol to polysaccharides, as well as oxidation of glycerol to glycolic acid and oxalic acid have been reported under microwave activation. Recently, the direct conversion of glycerol to acrylonitrile at 100° C. under microwave activation, where acrolein was the main product, has also been reported.

The intrinsic characteristics of glycerol, such as its low vapour pressure, high boiling point, high dielectric constant and polarity value make it a suitable solvent for microwave (MW) irradiation. Therefore, it was found, as described herein, that glycerol could be rapidly converted into AA and AF.

AF has several potential applications, such as it can be used as a solvent in spray lacquers, enamels, varnishes, and latex paints, and as an ingredient in paint thinners and strippers, varnish removers, and herbicides. It is used in liquid soaps, cosmetics, industrial and household cleaners, and dry-cleaning compounds. Further, polymerization of allyl esters under microwave conditions were investigated. Gels at relatively high conversion were obtained, which could be used as reactive plasticizers to improve the thermoplastics processing.

As described herein, the conversion of glycerol to allyl alcohol (AA), with an optional use of microwaves, and further esterification of AA to allyl formate was investigated.

The conversion of glycerol to AA using formic acid (FA) was studied in a CEM discover microwave reactor using open and closed vessel conditions, as well as conventional heating. Optimization of the reaction was carried out using statistical methods. Intermediate and final products were characterized using proton nuclear magnetic resonance ($^1$H-NMR), gas chromatography (GC) and Fourier transform infrared spectroscopy (FTIR). Rapid conversion of glycerol to AA was observed under microwave irradiation in the presence of FA. Particularly, addition of FA to preheated glycerol resulted in conversion into AA at lower temperatures and shorter time with higher purity as compared to conventional heating. This supported that glycerol could be rapidly converted to AA at lower temperatures using microwave irradiation.

Following the deoxydehydration (DODH) of glycerol to allyl alcohol (AA) AA was converted to allyl formate (AF) under solvent free conditions. AA and AF were then rapidly polymerized in a microwave seal-vessel. Products were characterized with IR spectroscopy, proton nuclear magnetic resonance, differential scanning calorimetry, and thermal analysis.

Materials and Methods
Conversion of Glycerol

Typically, glycerol (40 g, 0.43 mol, 82-100% purity) and formic acid (9.8 ml, 0.26 mol 98% purity) were charged into a 50 ml round bottom flask and placed in a microwave vessel. The flask was connected with a condenser set for downward distillation. Temperature within the reaction mixture was measured with an infrared temperature sensor. The temperature program involved ramping to 195° C., holding for one minute, ramping to 240° C., and holding 10 minutes. A fraction of the distillate was collected before 195° C. The fraction of distillate collected until 195° C. was separated from a fraction of distillate collected between 195° C. to 260° C. Once the mixture cooled to a temperature between 95 to 100° C., 7.0 ml (0.18 mol) of formic acid was added. Another distillation was carried out as described above. The reaction mixture was then cooled again, and a third portion of 7.0 ml of formic acid was added, following which a third distillation was carried out as described above. It was found that use of another type of acid, in place of formic acid, produced charring and very low yields.

The 195-260° C. fractions of the distillate were treated with potassium carbonate to salt out AA and to neutralize the formic acid present. The mixture was distilled in the microwave. AA was collected in a fraction of distillate up to 80° C. AA was then converted to AF as follows.

AA (20 ml, 0.3 mol) and formic acid (11.2 ml, 0.3 mol) were placed in a round bottom flask in the microwave vessel. The vessel was connected to a reflux system. The reaction was run at 60° C. for 30 min. Water was added to separate two layers, which were separated with a separatory funnel. The separated AF was used for further polymerization to poly (allyl formate). $^1$H-NMR was used to calculate yield and purity of each compound, AA (95% purity) and AF (90% purity).

Polymerizations

Polymerization of Allyl Alcohol: AA (4 ml, 0.06 mol) was purged with nitrogen (10 min solution, 10 min headspace) and then tert-butyl hydroperoxide 0.75 ml (0.004 mol) was added. The reaction was carried out in a microwave sealed vessel at 130° C. for 10 min.

Polymerization of Allyl Formate: AF (4 ml, 0.04 mol) was purged with nitrogen (10 min solution, 10 min headspace) and then tert-butyl hydroperoxide 0.75 ml (0.004 mol) was added. The reaction was microwave sealed vessel at 130° C. for 20 min at 100 PSI.

Characterization

Infrared spectra were recorded at room temperature in the region of 400-4000 cm$^{-1}$ at 16 scans and resolution of 4 cm$^{-1}$ with a Bruker Alpha FTIR spectrophotometer (Bruker Optics, Esslingen, Germany) equipped with a single-bounce diamond ATR crystal. FT-IR samples for allyl alcohol monitoring were collected every minute, and kept cold until analysis the same day of reaction. For allyl formate monitoring, samples were collected every five minutes and analyzed immediately. Gel permeation chromatography of the polymers was carried out on the system equipped with styragel HR1 GPC column and detector (ELSD2000s, Santa Clara, Calif., USA). The injected volume of sample was 10 μL with 0.5 mg/mL. THF was used as eluent at a flow rate of 0.5 mL/min. Differential Scanning calorimetry (DSC) analysis was performed on calorimetric apparatus (2920 Modulated DSC, TA Instrument, USA) under a stream of nitrogen gas. Pure indium sample was used to calibrate heat flow and temperature of the instrument. All samples were scanned in a temperature range of −50-50° C. at a heating rate of 5° C. per minute. Thermogravimetric analyses of all polymers were performed on TGA Q50 (TA Instrument, USA) under a flow of nitrogen gas. Analyses were performed by heating samples in a temperature range of 25-600° C. with heating rate of 10° C. per minute. Proton nuclear magnetic resonance CH NMR) samples were recorded on a Agilent/Varian Inova three-channel 400 MHz spectrometer. Spectra were recorded in 5 mm NMR tubes. 3-(Trimethylsilyl)-1-propanesulfonic acid sodium salt was used as internal standard for $^1$H NMR quantitation.

Results and Discussion
Microwave-Assisted Distillation

DODH of glycerol was carried out in a microwave-assisted distillation, and in a sand bath for comparison purpose (FIG. 1). At first, the sand bath distillation (210° C., 1819 min) for DODH of glycerol to AA under conventional heating was carried out and required several hours to reach completion (Table 1, entry 1). The reaction was followed by FT-IR showing amounts of starting material still left during the reaction.

Figure 2:
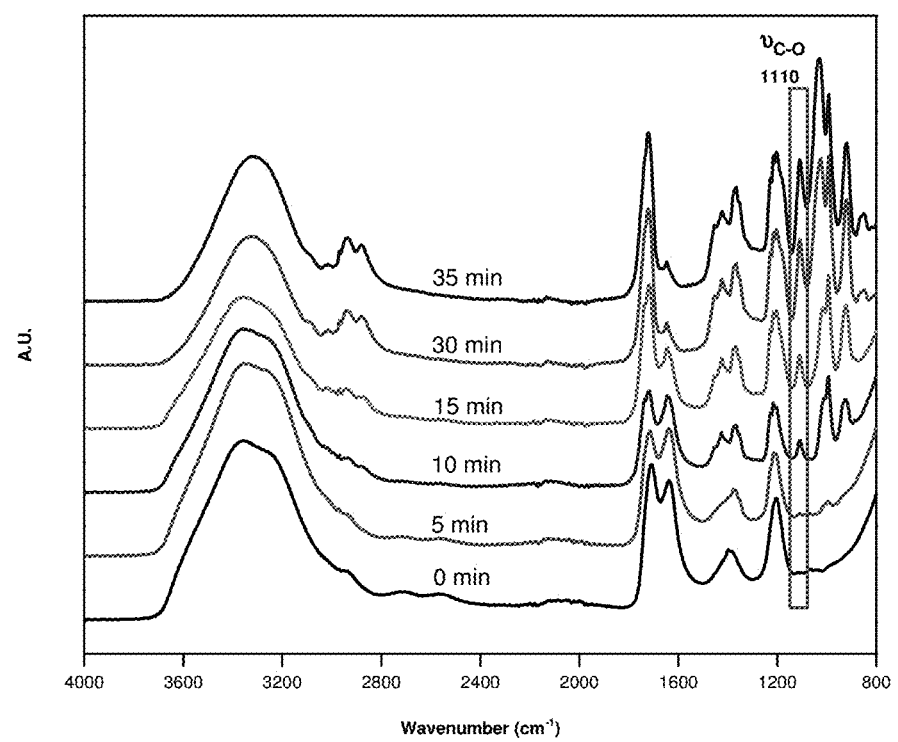
FIG. 2 depicts FT-IR spectra monitoring for deoxydehydration of glycerol to allyl alcohol assisted by formic acid I-every 5 minutes, and II-intensity of alkoxy band 1110 cm$^{-1}$.
Figure 2:
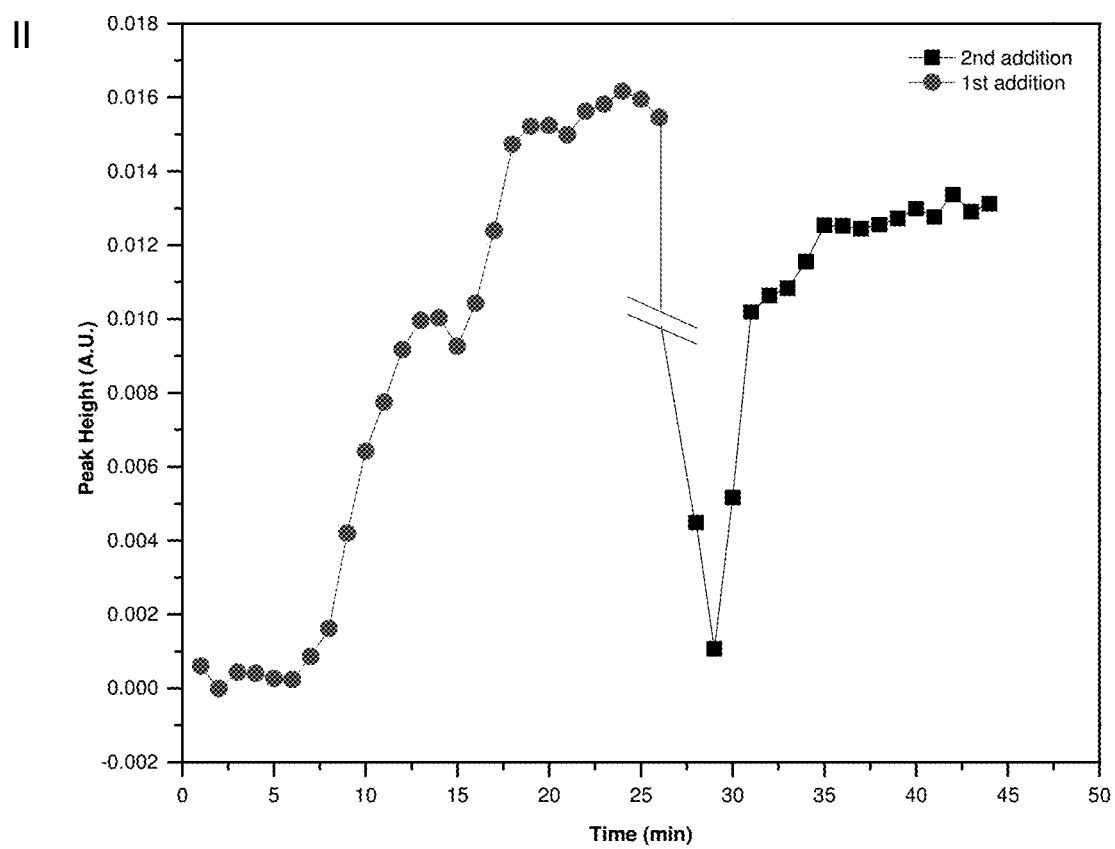

The microwave-assisted DODH of glycerol was carried out in an open-vessel connected to a distillation system (240° C., 54 min) (Table 1, entry 2) with continuous removal of AA from the reaction mixture through distillation. FIG. 2 depicts rapid conversion to AA using direct microwave heating through sequential additions of formic acid. Intensity of the alkoxy band of allyl alcohol ($v_{C-O}$=1110 cm$^{-1}$) as a function of time increased, and a maximum yield of allyl alcohol occurred between 15 and 25 minutes after distillation started. After a second addition of formic acid was added, only 10 minutes was required for allyl alcohol to start to distill again

TABLE 1

Comparison of the energy consumed by sand bath and microwave for the DODH of glycerol.

| Entry | Heating method | Glycerol (mol) | Formic acid (mol) | Yield (%) | $t_R$ (min) | Energy (KWh) |
|---|---|---|---|---|---|---|
| 1 | MW | 0.4 | 0.5 | 61 | 54 | 0.342 |
| 2 | Sand bath | 0.4 | 0.5 | 45 | 1819 | 5.672 |

Figure 3:
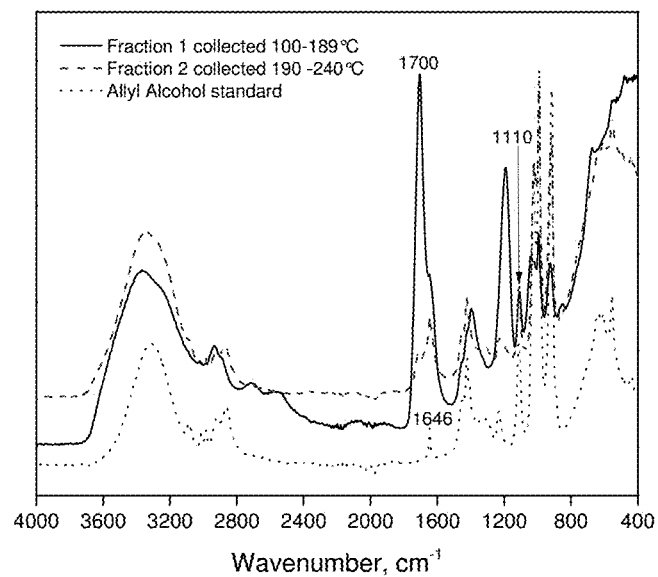
FIG. 3 depicts FT-IR spectra of AA (standard) and distilled collected during microwave-assisted distillation.
Figure 4:
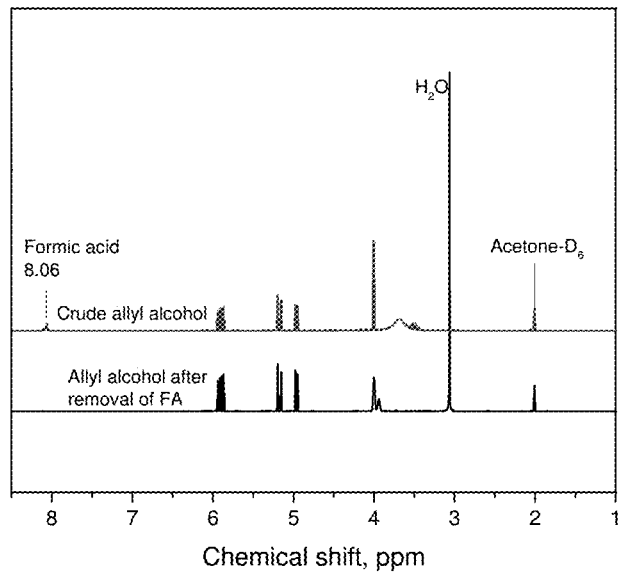
FIG. 4 depicts $^1$H-NMR spectra of crude distilled of AA and purified AA after K$_2$CO$_3$ treatment.

As is apparent from the FT-IR spectra (FIG. 3), the broad peak at 1700 cm$^{-1}$ is a characteristic band for the C=O of formic acid, because fraction 1 has formic acid as a major product. As the temperature increased, this peak was considerable decreased and the alkenyl C=C stretch (fraction 2, 1646 cm$^{-1}$) was more evident. The $^1$H-NMR spectra confirmed removal of formic acid collected during the second fraction (FIG. 4), as per the peak at 8.06 in the crude distillate that disappeared after purification with K$_2$CO$_3$.

Microwave-Assisted Conversion of AA to AF

Figure 5:
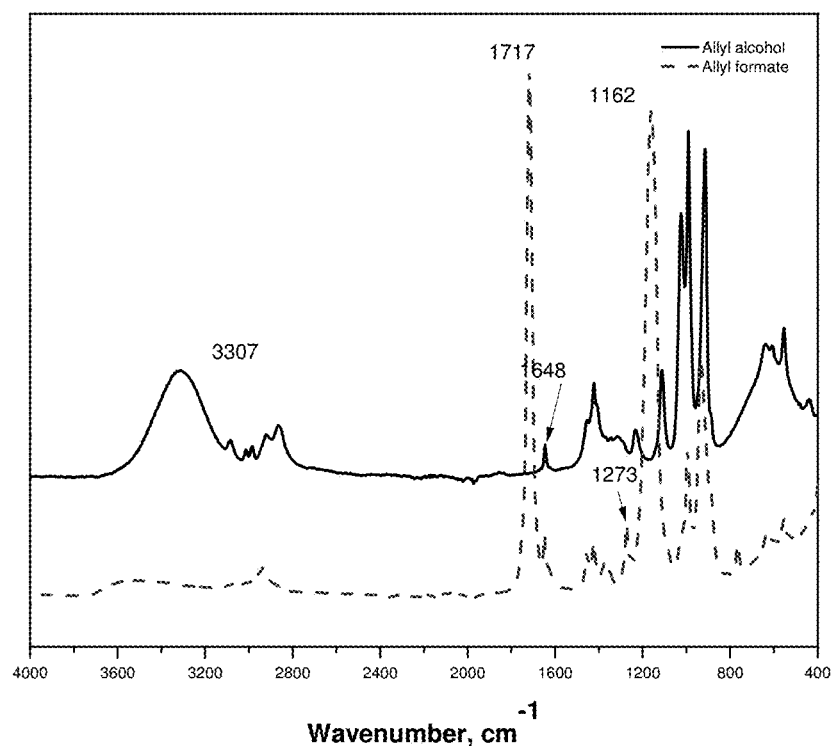
FIG. 5 depicts a FT-IR spectral comparison of AA (top) and AF (bottom).

Esterification of AA to AF was carried out using open-vessel microwave under reflux (60° C., 30 min). Water was added to the mixture after reaction and two layers were formed. The top layer was AF and the bottom layer contained unreacted reagents. FT-IR (FIG. 5) analysis confirmed formation of AF with new peaks at 1162, 1273, 1648, and 1717 cm$^{-1}$. The peak related to O—H band (3307 cm$^{-1}$) disappeared after the two layers separation.

Figure 6:
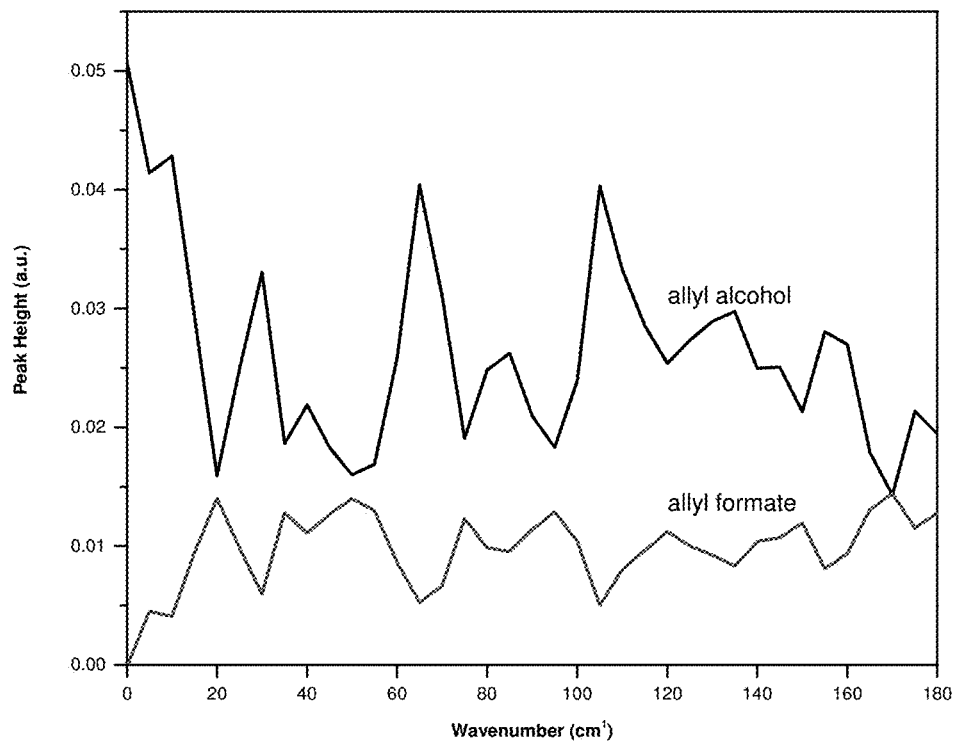
FIG. 6 depicts FT-IR spectra monitoring of the intensity of band 1273 during esterification of allyl alcohol and formic acid to allyl formate under conventional heating at 100° C.

Allyl formate was studied under conventional heating to facilitate the sampling of products during reaction. Samples were taken every five minutes and measured immediately. The acyl vibration band of allyl formate ($v_{C-O}$=1273 cm$^{-1}$) and the alkyl band of allyl alcohol were monitored. FIG. 6 shows after 20 minutes of reaction a higher yield of allyl formate and a reduction of intensity of the characteristic band of allyl alcohol ($v_{C-O}$=1110 cm$^1$). As the reaction evolved overtime, the equilibrium of the reaction was displaced to constantly shifting allyl formate to allyl alcohol and vice versa.

Figure 7:
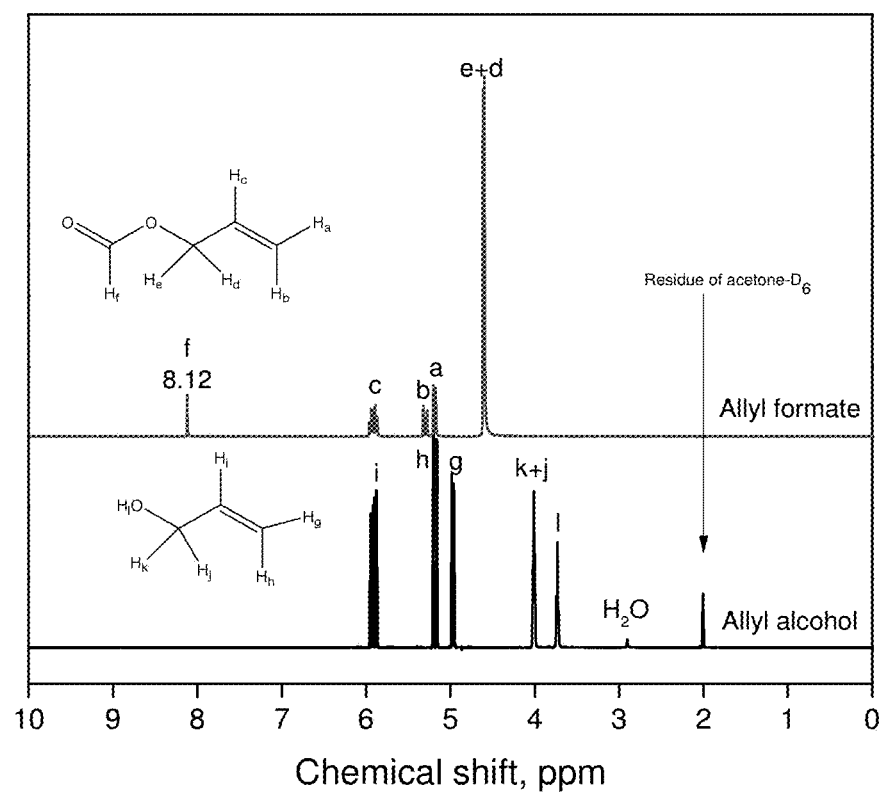
FIG. 7 depicts a $^1$H-NMR spectral comparison of AA and allyl formate in d$_6$-acetone.
Figure 8:
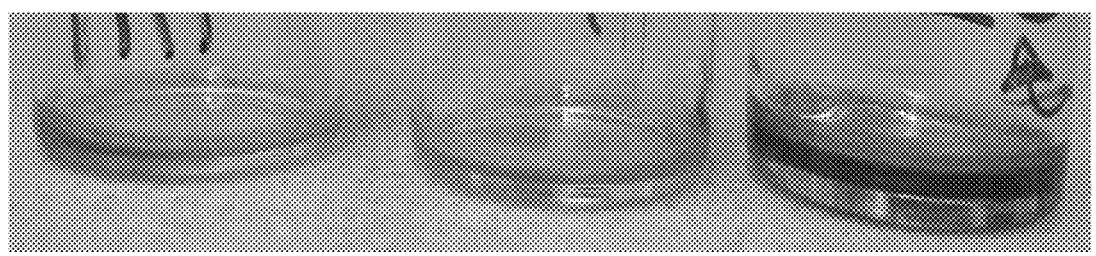
FIG. 8 depicts PAA after drying, Table 2, entry 2, 3, and 4 from left to right (a, b, and c), respectively, wherein the PAA were light yellow to dark orange depending on reaction conditions.
Figure 9:
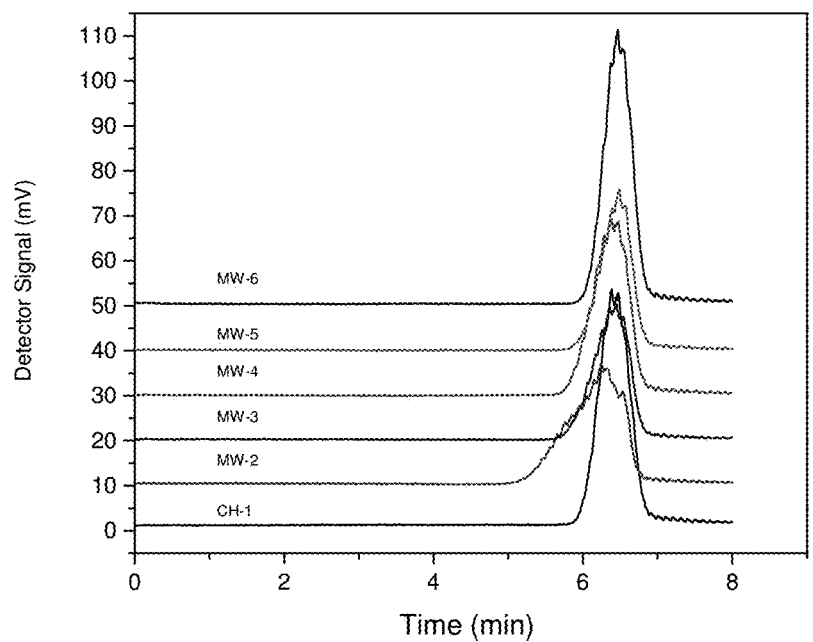
FIG. 9 depicts GPC traces of polymers (Table 2, entry 1-6).

These results were corroborated by $^1$H-NMR analysis (FIG. 7). The terminal H (H$_f$, 8.12) was in the spectrum of the allyl formate.

Polymerization of AA to Poly(Allyl) Alcohol

Figure 10:
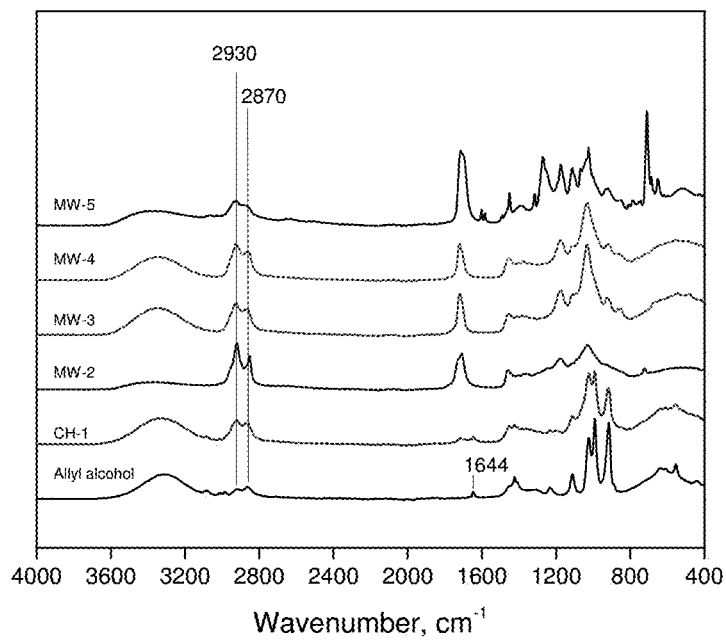
FIG. 10 depicts a FT-IR spectral comparison of PAA (bottom) under different conditions and AA. (CH) conventional heating (second from bottom), (MW) microwave.
Figure 11:
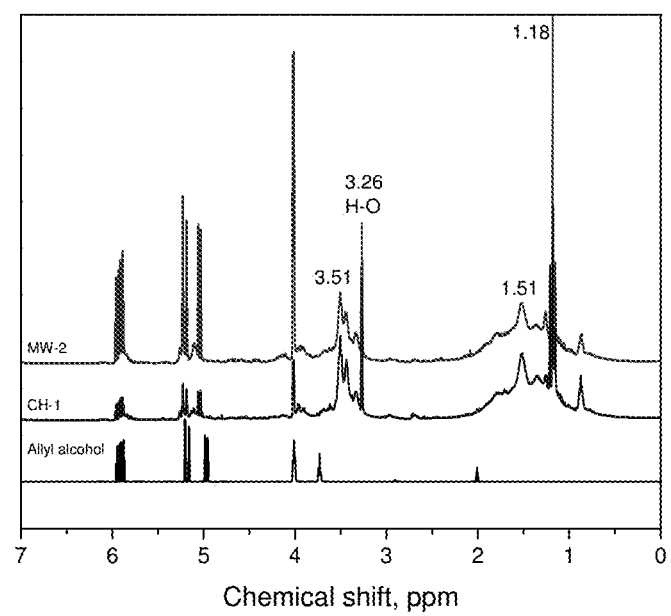
FIG. 11 depicts $^1$H-NMR spectra of selected polymers in CD$_3$OD (Table 2, entry 1-2; AA-bottom, CH-1 top).

Polymerization of allyl alcohol was performed in a microwave, solvent free, by a radical initiator mechanism. Reactions were carried out at 130° C. under nitrogen in a seal tube using as initiator tert-butyl hydroperoxide or benzoyl peroxide. Polymerization results are collected in Table 2.

indicating some monomer left in after polymerization (FIG. 10). $^1$H-NMR spectra of the polymers in CD$_3$OD solution were also obtained and peaks at 1.18, 1.51, 3.36, and 3.54 ppm for methylene and methyl moieties of the main chain, and hydroxyl and methylene moieties of the side chain, respectively were observed (FIG. 11).

Figure 12:
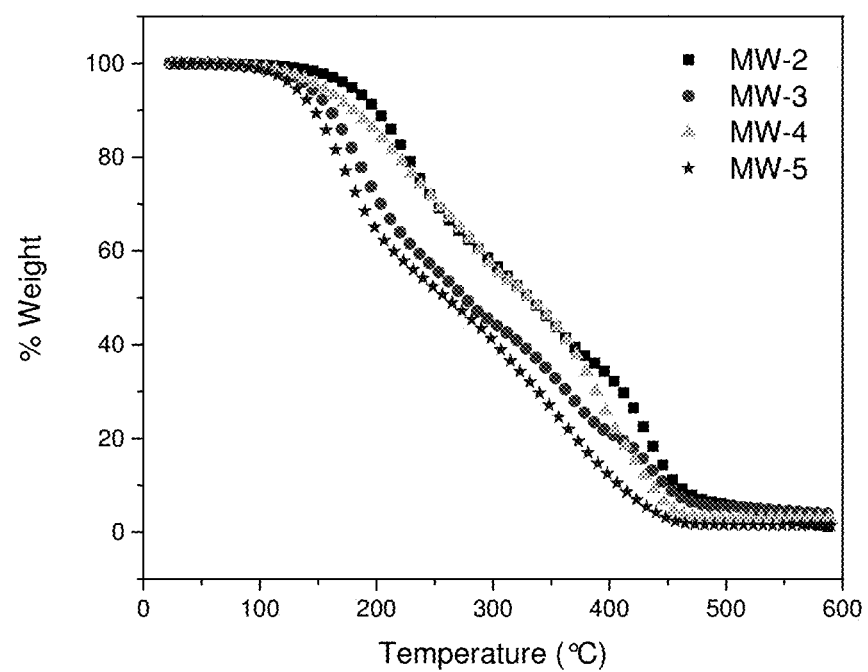
FIG. 12 depicts I—a TGA and DTG spectral comparison of polymers (Table 2, entry 2-5); II—DTG spectral comparison of polymers (Table 2, entry 2-5).
Figure 12:
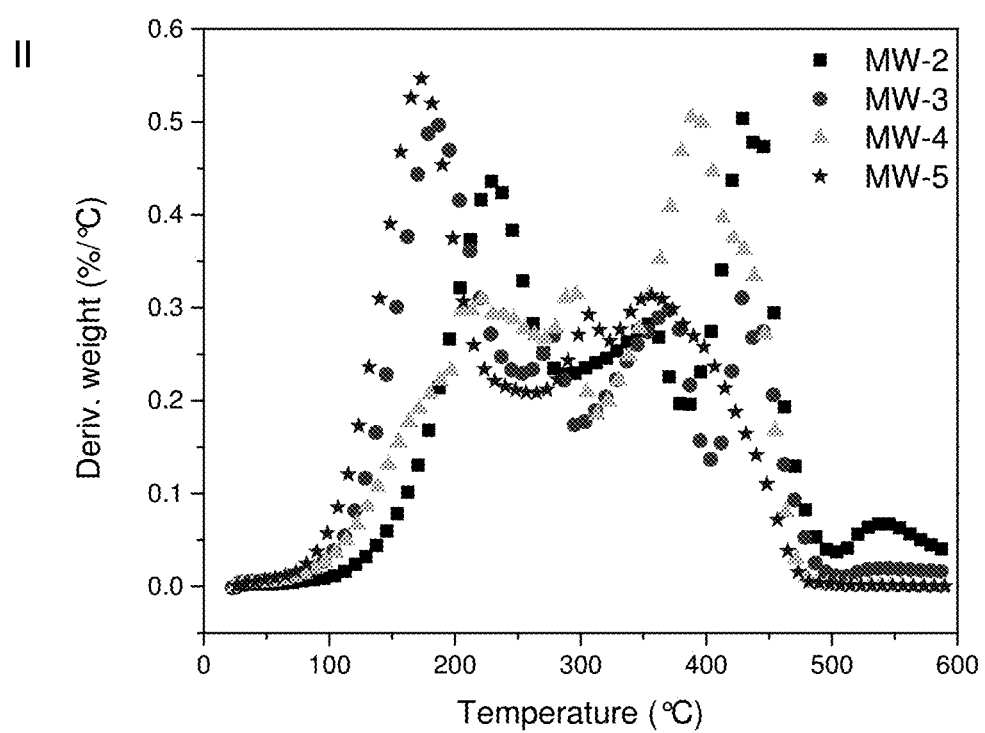

AA polymerized to give a molecular weight (M$_w$=2531 g/mol) higher than previously reported [Laible R. Chemical Reviews, 1958. 58 (5): p. 807-843.]. It was found that the yield % increased with reaction time. Degradation and thermal stability behavior of the polymers were studied by TG (thermogravimetric) and DTG (derivative thermogravimetric) (FIG. 12). The major weight loss (%) of all polymers was in the temperature range of 170-230° C. The polymer labeled as entry 5 showed an initial weight lost starting at 170° C., while the polymer of entry 2 started at 230° C., which could be attributed to a difference in the polymer's molecular weights. DTG curves of polymers showed the temperature where maximum weight loss (T$_{max}$) was observed. Polymers underwent different weight loss during the analyses.

Figure 13:
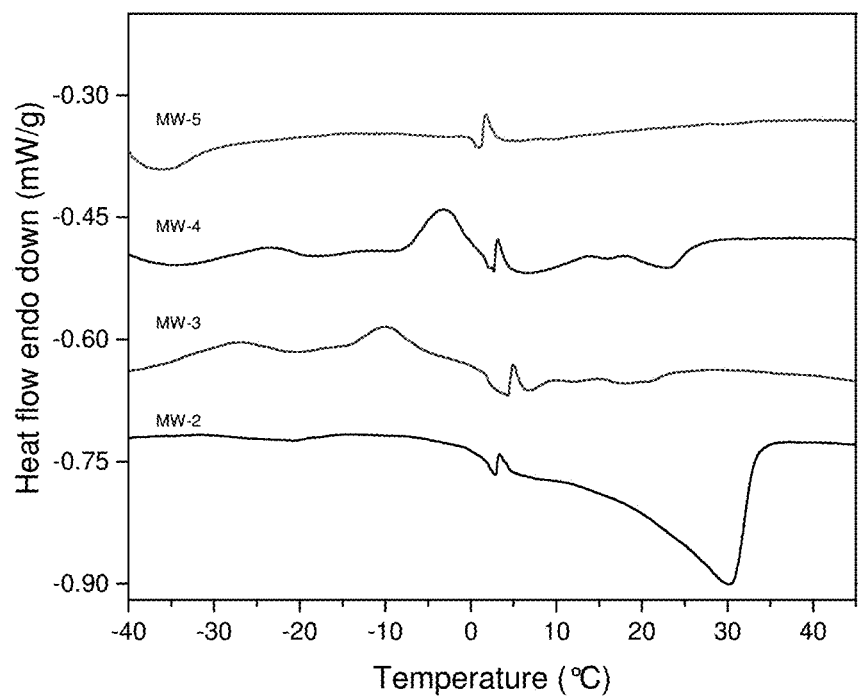
FIG. 13 depicts DSC thermograms of polymers (Table 2, entry 2-5; MW-2 bottom, MW-5 top, MW-3 second from bottom).
Figure 14:
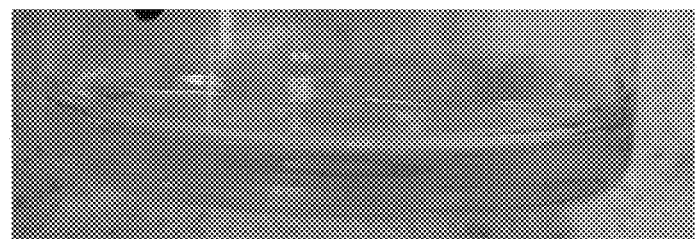
FIG. 14 depicts polyallylformate (PAF) after drying, wherein the PAF had a light yellow color.
Figure 15:
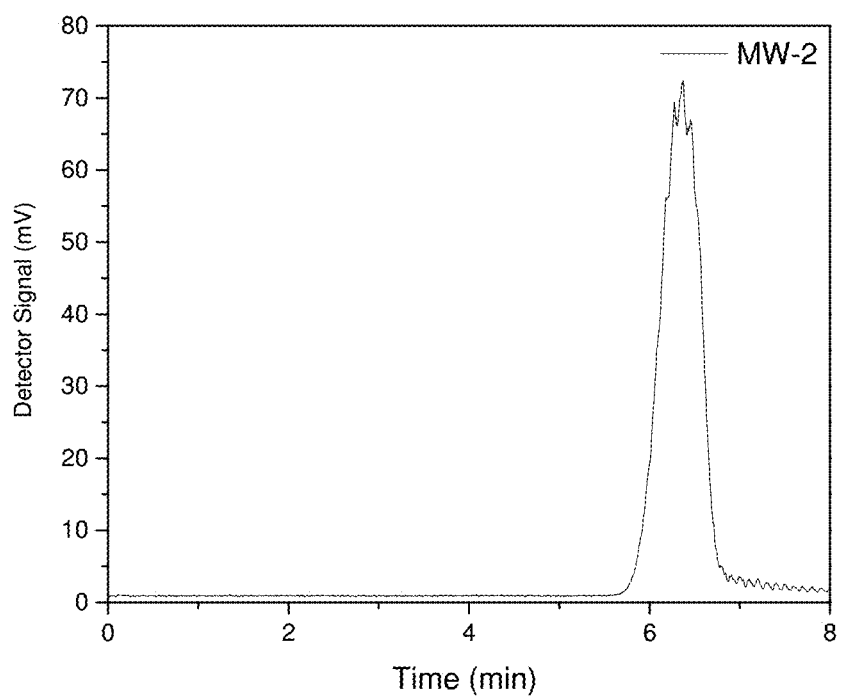
FIG. 15 depicts GPC spectrum of polymer (Table 3, entry 2).
Figure 16:
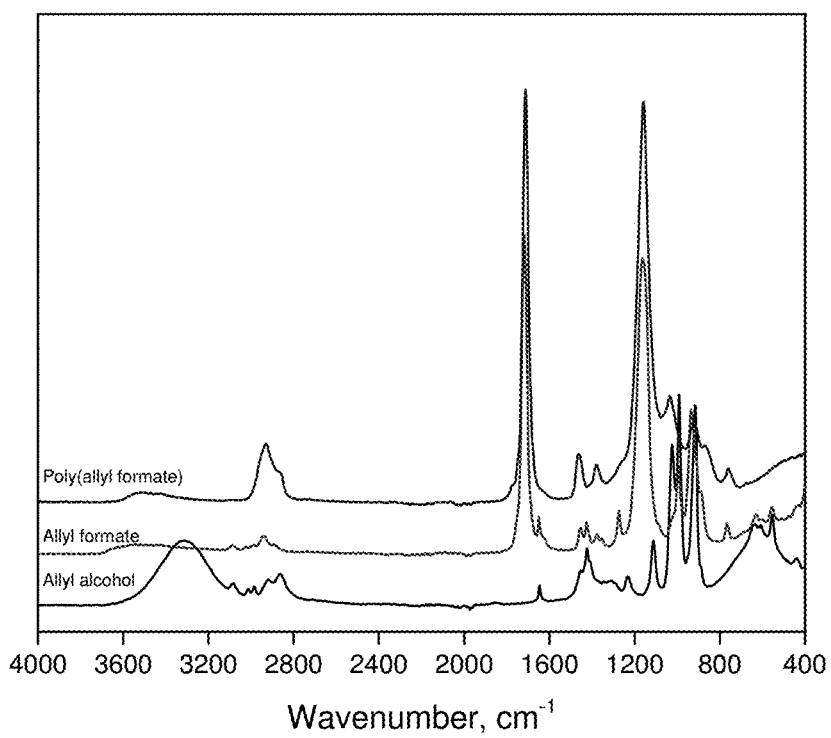
FIG. 16 depicts FT-IR spectra of polymers (Table 3, entry 2; AA bottom, PAF top).
Figure 17:
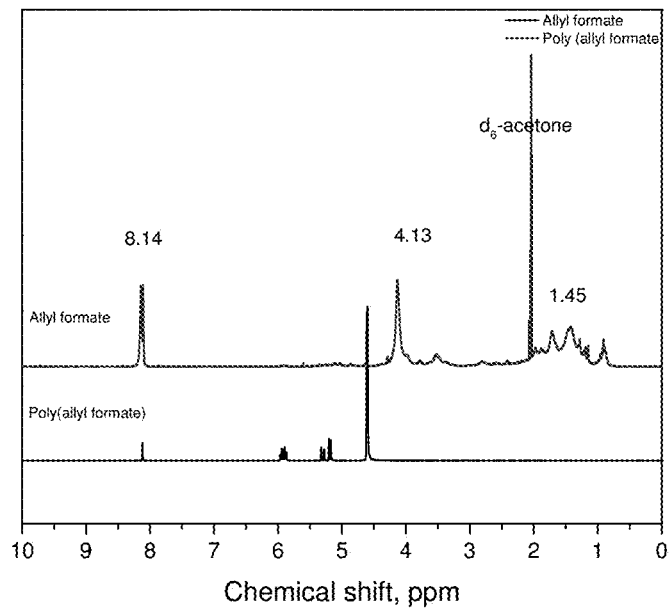
FIG. 17 depicts $^1$H-NMR spectra of selected polymers in CD$_3$OD (Table 3, entry 2; AA bottom).
Figure 18:
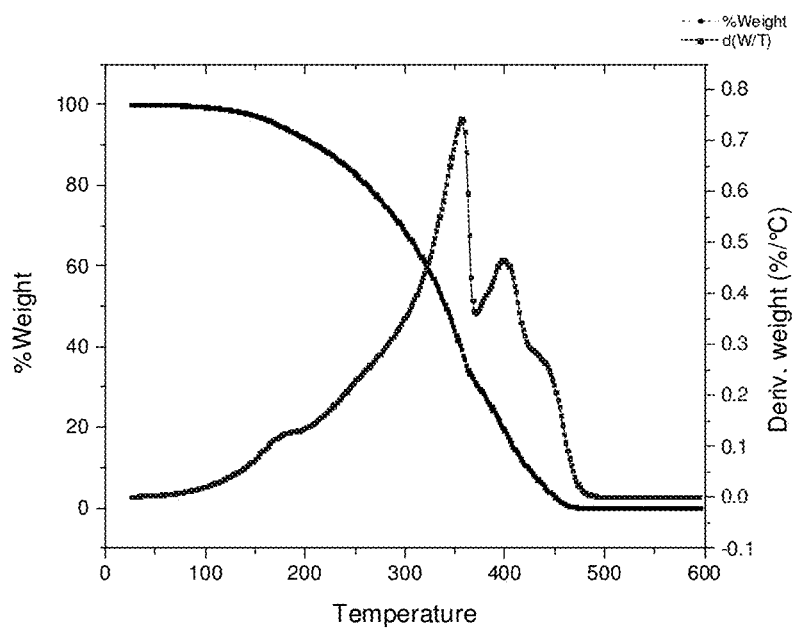
FIG. 18 depicts TGA and DTG spectra comparison of polymers (Table 3, entry 2).
Figure 19:
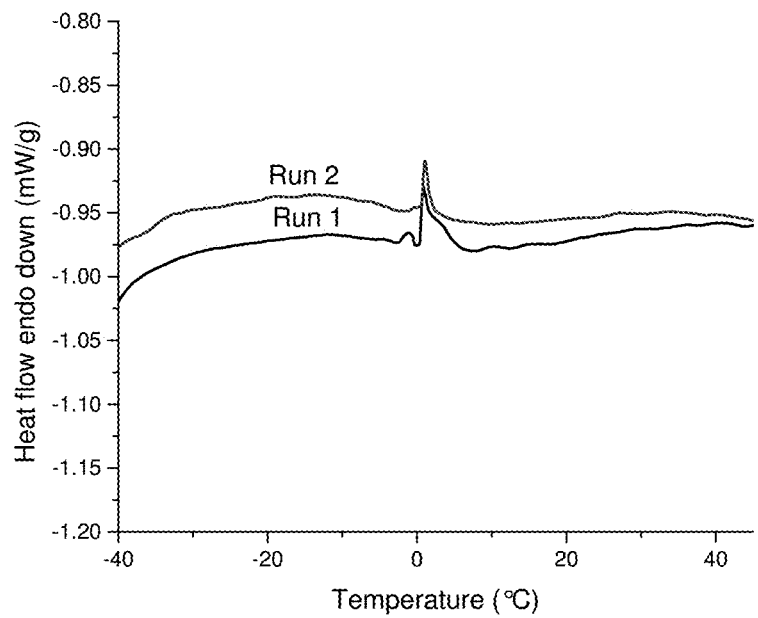
FIG. 19 depicts DSC thermograms of polymers (Table 3, entry 2).

DSC thermograms were also run (FIG. 13). The plots showed the 2$^{nd}$ heating run of the selected polymers. The polymers of entries 2-5 generally showed transition before −20° C., which could be the glass transition. All polymers had a crystallization peak and melting peak between 0-5° C., indicating the polymers crystallized. Polymer (entry 2) with a higher molecular weight underwent a big endothermic change with T$_{max}$=30° C.

Polymerization of Allyl Formate to Poly (Allyl Formate)

Allyl formate was polymerized with tert-butyl hydroperoxide (Table 3). When polymerization of the monomer was undertaken in a sealed-vessel at atmospheric pressure, no conversion occurred (Table 3, entry 1). Once the pressure was 100 PSI, with the same conditions, a yellow viscous solution was obtained (Table 3, entry 2). FT-IR analysis confirmed the polymerization. A band at C=C (1646 cm$^{-1}$) disappeared in FT-IR spectra of the polymer, while a C=O

TABLE 2

Polymerization of allyl alcohol (AA) initiated by tert-butyl hydroperoxide (tBuOOH) and benzoyl peroxide (BPO) (a) silicon oil and (b) microwave.

| Entry | Monomer | Initiator | M/I | Condition | Temperature (° C.) | Time (min) | M$_w$ (g/mol) |
|---|---|---|---|---|---|---|---|
| 1$^a$ | AA | tBuOOH | 100/6 | N$_2$ | 130 | 480 | 941 |
| 2$^b$ | AA | tBuOOH | 100/6 | N$_2$ | 130 | 10 | 2531 |
| 3$^b$ | AA | tBuOOH | 100/6 | N$_2$ | 130 | 10 | 1155 |
| 4$^b$ | AA | tBuOOH | 100/6 | N$_2$ | 130 | 20 | 1169 |
| 5$^b$ | AA | BPO | 100/4 | N$_2$ | 130 | 20 | 906 |
| 6$^b$ | AA | tBuOOH | 100/6 | N$_2$ | 60, 100 | 30, 15 | 806 |

The isolated polymer was analyzed by IR spectroscopy, NMR spectroscopy, TGA, and DSC. The characteristic band in the IR spectra at 1644 cm$^{-1}$, a sign of unsaturation, generally disappeared but was observed in some polymers band (1710 cm$^{-1}$) increased in intensity. $^1$H-NMR spectra of the polymer in d$_6$-acetone solution were acquired and peaks at 1.45, 4.13, and 8.14 were observed. The molecular weight (Mw=1198) is the same order of the PAA polymers.

TABLE 3

Polymerization of allyl formate (AF) initiated by tert-butyl hydroperoxide on microwave in open vessel connected to reflux system in solvent free.

| Reaction number | Monomer | Initiator | M/I | Condition | Pressure (PSI) | Temperature (° C.) | Time (min) | Mw (g/mol) |
|---|---|---|---|---|---|---|---|---|
| 1 | AF | tBuOOH | 100/8 | N$_2$ | 0 | 130 | 20 | — |
| 2 | AF | tBuOOH | 100/8 | N$_2$ | 100 | 130 | 20 | 1198 |

The initial weight loss of the polymer was after 170° C. Compared with the polymers from the AA monomer, the maximum weight loss temperature of the allyl formate polymer was at a higher temperature (356° C.). By 600° C., the polymer had losses of 100% in weight.

Statistical Optimization of Glycerol Conversion

The experimental design and statistical analysis were carried out using the Design Expert software (11.1.1.0, Stat-Ease, Inc., USA). The degree of experiments chosen was Box-Behnken design (BBD), 17 experiments were designed with five center points and twelve middle points of the edges three independent variable that could potentially influence the efficiency of the process were chosen at three levels: temperature (200, 230, 260° C.), molar ratio glycerol: formic acid (FA:Gly) (0.6:1, 1.2:1, 1.8:1), and irradiation time (10, 20, 30 min).

To study the mathematic relationship between the three independent variables and the responses, a quadratic polynomial equation was used (Equation 1). A multiple regression analysis was performed to obtain the coefficients and solved the equations to predict the responses.

$$Y=\beta_0+\beta_1 X_1+\beta_2 X_2+\beta_3 X_3+\beta_{12} X_1 X_2+\beta_{13} X_1 X_3+ \beta_{23} X_2 X_3+\beta_{11} X_1^2+\beta_{22} X_2^2+\beta_{33} X_3^2 \quad \text{(Eq. 1)}$$

Where,
Y estimate response
$\beta_0$ constant
$\beta_1$, $\beta_2$, $\beta_3$ linear coefficients
$\beta_{12}$, $\beta_{13}$, $\beta_{23}$ interaction coefficients between the three factors
$\beta_{11}$, $\beta_{22}$, $\beta_{33}$ quadratic coefficients In agreement with previous studies and our trial experiments, temperature, time and glycerol:formic acid ratio are three variables that could potentially affect the yield percent of allyl alcohol and allyl formate. In order to obtain the optimum conditions and study the interaction effects of the three variables, experiments were carried out using BBD.

The experimental data was fitted in linear, two factor interaction, quadratic, and cubic models in order to evaluate the best model that lead to logical and consistent results. Table 4 shows the comparison among the different models and their comparison between three different tests: sequential model sum of squares, lack of fit tests, and model summary statistics. Based on the results of the $R^2$, adjusted $R^2$, predicted $R^2$, and the standard deviation, the quadratic model was the best model fitted for % yield of allyl alcohol.

TABLE 4

Sequential model fitting for yield percent of allyl alcohol.

Sequential Model Sum of Squares

| Source | Sum of Squares | df | Mean Square | F-value | p-value | |
|---|---|---|---|---|---|---|
| Mean vs Total | 28843.92 | 1 | 28843.92 | | | |
| Linear vs Mean | 332.53 | 3 | 110.84 | 6.07 | 0.0082 | |
| 2FI vs Linear | 165.38 | 3 | 55.13 | 7.65 | 0.0060 | |
| Quadratic vs 2FI | 71.14 | 3 | 23.71 | 188.41 | <0.0001 | Suggested |
| Cubic vs Quadratic | 0.6672 | 3 | 0.2224 | 4.16 | 0.1011 | Aliased |
| Residual | 0.2138 | 4 | 0.0535 | | | |
| Total | 29413.85 | 17 | 1730.23 | | | |

TABLE 4-continued

Sequential model fitting for yield percent of allyl alcohol.

Lack of Fit Tests

| Source | Sum of Squares | df | Mean Square | F-value | p-value | |
|---|---|---|---|---|---|---|
| Linear | 237.18 | 9 | 26.35 | 492.95 | <0.0001 | |
| 2FI | 71.81 | 6 | 11.97 | 223.86 | <0.0001 | |
| Quadratic | 0.6672 | 3 | 0.2224 | 4.16 | 0.1011 | Suggested |
| Cubic | 0.0000 | 0 | | | | Aliased |
| Pure Error | 0.2138 | 4 | 0.0535 | | | |

Model Summary Statistics

| Source | Std. Dev. | $R^2$ | Adjusted $R^2$ | Predicted $R^2$ | PRESS | |
|---|---|---|---|---|---|---|
| Linear | 4.27 | 0.5835 | 0.4873 | 0.1658 | 475.44 | |
| 2FI | 2.68 | 0.8736 | 0.7978 | 0.5075 | 280.68 | |
| Quadratic | 0.3548 | 0.9985 | 0.9965 | 0.9807 | 11.01 | Suggested |
| Cubic | 0.2312 | 0.9996 | 0.9985 | | | Aliased |

The model was evaluated based on the experimental data to check if the estimated model would provide logical results.

The actual and predicted values are shown in Table 5, as well as the coded matrixes for allyl alcohol and allyl formate yield (%).

TABLE 5

Box-Behnken design matrix for coded values and experimental and predicted values for allyl alcohol, allyl formate, and total yield (%).

| | Coded values[a] | | | Allyl alcohol % yield | | Allyl formate % yield | |
|---|---|---|---|---|---|---|---|
| | $X_1$ | $X_2$ | $X_3$ | Experimental | Predicted | Experimental | Predicted |
| 1 | 1 | 1 | 0 | 48.93 | 49.21 | 2.34 | 2.34 |
| 2 | 0 | 0 | 0 | 43.39 | 43.29 | 2.01 | 2.00 |
| 3 | -1 | 0 | -1 | 33.49 | 33.52 | 2.14 | 2.12 |
| 4 | 0 | 0 | 0 | 43.34 | 43.29 | 2.01 | 2.00 |
| 5 | 0 | 1 | -1 | 47.62 | 47.29 | 2.55 | 2.55 |
| 6 | -1 | 1 | 0 | 35.20 | 35.49 | 2.67 | 2.69 |
| 7 | 1 | 0 | 1 | 39.93 | 39.89 | 1.95 | 1.97 |
| 8 | 0 | -1 | 1 | 35.59 | 35.92 | 1.24 | 1.24 |
| 9 | 0 | 0 | 0 | 43.24 | 43.29 | 2.00 | 2.00 |
| 10 | -1 | -1 | 0 | 31.75 | 31.47 | 1.18 | 1.19 |
| 11 | -1 | 0 | 1 | 42.41 | 42.36 | 2.24 | 2.24 |
| 12 | 1 | 0 | -1 | 54.52 | 54.57 | 5.47 | 5.04 |
| 13 | 0 | -1 | -1 | 35.86 | 36.10 | 1.7 | 2.04 |
| 14 | 0 | 1 | 1 | 41.87 | 41.63 | 6.77 | 6.43 |
| 15 | 0 | 0 | 0 | 43.56 | 43.29 | 3.77 | 4.04 |
| 16 | 1 | -1 | 0 | 36.62 | 36.32 | 1.86 | 1.95 |
| 17 | 0 | 0 | 0 | 42.94 | 43.29 | 3.71 | 4.04 |

Fitting of Second Order Polynomial Equation for % Yield Allyl Alcohol

When response ratio is greater than 10, usually a transformation is require, in the case of allyl alcohol response ratio was only 1.72, where no transformation was require. After fitting the data to the quadratic model, the equation explained the relationship among independent variables and their significant in the system.

$$Y(AA)=-154.46807+1.11870*T+8.34504*r- 4.35326*t+0.123183*T*r-0.019593*T*t- 0.228414*r*t-0.001565*T^2-10.44331*r^2+ 0.007031*t^2 \quad \text{(Eq. 2)}$$

A, B, C, AB, AC, BC, $A^2$, $B^2$, $C^2$ as all the p-value are <0.0001, means the model is significant, as well all the model terms.

Fitting of Second Order Polynomial Equation for % Yield Allyl Formate

Allyl formate is produced as a by-product during the DODH of glycerol towards the allyl alcohol. With the optimization of the conditions T, r, and t, we would like to reduce the AF.

The ratio response of % yield allyl formate is 5.14. When the initial model is fitted without any transformation and the ANOVA is applied, the Box-Cox test suggest to apply a square root with a $\lambda=0.5$, being the final equation fitting quadratic the equation below.

$$\text{Sqrt}Y(AF) = +0.585221 - 0.013008*T + 3.68161*r + 0.027713*t - 0.007615*T*r - 0.000328*T*t + 0.006876*r*t + 0.000060*T^2 - 0.436331*r^2 + 0.000881*t^2 \quad \text{(Eq. 3)}$$

Statistical Analysis

After the model selected based on the fitting of the experimental data, an analysis of variances (ANOVA) was applied to evaluate the model and the significant of each model term based on the p-value. The p-values of the both equations, AA and AF, indicate that linear, quadratic, and interactive coefficients are significant terms in the models, as shown in Table 6.

In the case of allyl alcohol % yield, the model F-value of 502.36 indicates the model is significant. The lack of fit F-value of 4.16 and the correspondent p-value of 0.1011 was not significant as it was smaller than the pure error of 0.2138. The determination coefficient ($R^2$), adjusted determination coefficient ($R_\alpha^2$), and the predicted determination coefficient ($R_p^2$) were also considered to evaluate the fitting of the model. As can be seen in Table 4, the $R^2=0.9985$ of the quadratic model indicates the model has a good fit. The adjusted determination coefficient ($R_\alpha^2$), and the predicted determination coefficient ($R_p^2$) are also in agreement, as is suggested both should be within 0.20 of each other, otherwise there may be a problem with either the data or the model.

In the case of allyl alcohol % yield, the model F-value of 502.36 indicates the model is significant. The lack of fit F-value of 4.16 and the correspondent p-value of 0.1011 was not significant as it was smaller than the pure error of 0.2138. The determination coefficient ($R^2$), adjusted determination coefficient ($R_\alpha^2$), and the predicted determination coefficient ($R_p^2$) were also considered to evaluate the fitting of the model. As can be seen in Table 4, the $R^2=0.9985$ of the quadratic model indicates the model has a good fit. The adjusted determination coefficient ($R_\alpha^2$), and the predicted determination coefficient ($R_p^2$) are also in agreement, as is suggested both should be within 0.20 of each other, otherwise there may be a problem with either the data or the model.

TABLE 6

ANOVA regression moel for the prediction of AA and AF % Yield

| Source | Sum of squares | Degree of freedom | Mean square | F value | p-value | |
|---|---|---|---|---|---|---|
| Allyl alcohol | | | | | | |
| Model | 569.05 | 9 | 63.23 | 502.36 | <0.0001 | significant |
| $X_1$ | 172.55 | 1 | 172.55 | 1370.95 | <0.0001 | |
| $X_2$ | 142.94 | 1 | 142.94 | 1135.65 | <0.0001 | |
| $X_3$ | 17.04 | 1 | 17.04 | 135.42 | <0.0001 | |
| $X_1 X_2$ | 19.67 | 1 | 19.67 | 156.25 | <0.0001 | |
| $X_1 X_3$ | 138.20 | 1 | 138.20 | 1098.01 | <0.0001 | |
| $X_2 X_3$ | 7.51 | 1 | 7.51 | 59.69 | 0.0001 | |
| $X_1^2$ | 8.35 | 1 | 8.35 | 66.36 | <0.0001 | |
| $X_2^2$ | 59.51 | 1 | 59.51 | 472.85 | <0.0001 | |
| $X_3^2$ | 2.08 | 1 | 2.08 | 16.54 | 0.0048 | |
| Residual | 0.8810 | 7 | 0.1259 | | | |
| Lack of fit | 0.6672 | 3 | 0.2224 | 4.16 | 0.1011 | not significant |
| Pure error | 0.2138 | 4 | 0.0535 | | | |
| Cor Total | 569.93 | 16 | | | | |
| Allyl formate | | | | | | |
| Model | 3.29 | 9 | 0.3651 | 2392.20 | <0.0001 | significant |
| $X_1$ | 0.0113 | 1 | 0.0113 | 74.23 | <0.0001 | |
| $X_2$ | 3.00 | 1 | 3.00 | 19646.78 | <0.0001 | |
| $X_3$ | 0.0141 | 1 | 0.0141 | 92.10 | <0.0001 | |
| $X_1 X_2$ | 0.0752 | 1 | 0.0752 | 492.47 | <0.0001 | |
| $X_1 X_3$ | 0.0387 | 1 | 0.0387 | 253.50 | <0.0001 | |
| $X_2 X_3$ | 0.0068 | 1 | 0.0068 | 44.61 | 0.0003 | |
| $X_1^2$ | 0.0121 | 1 | 0.0121 | 79.56 | <0.0001 | |
| $X_2^2$ | 0.1039 | 1 | 0.1039 | 680.69 | <0.0001 | |
| $X_3^2$ | 0.0327 | 1 | 0.0327 | 214.18 | <0.0001 | |
| Residual | 0.0011 | 7 | 0.0002 | | | |
| Lack of fit | 0.0007 | 3 | 0.0002 | 2.96 | 0.1612 | not significant |
| Pure error | 0.0003 | 4 | 0.0001 | | | |
| Cor Total | 3.29 | 16 | | | | |

In case of the model of the allyl formate, the determination coefficient has a value of 0.9985. The difference between the adjusted and predicted determination coefficient for the allyl formate model is also <0.2, suggesting an adequate agreement between the model and the data.

TABLE 6

The determination coefficient ($R^2$), adjusted determination coefficient ($R_\alpha^2$), and the predicted determination coefficient ($R_p^2$) for AA PY and AFPY.

| | $R^2$ | Adjusted $R^2$ | Predicted $R^2$ | Mean ± SD | CV, % | Adequate precision |
|---|---|---|---|---|---|---|
| Allyl alcohol | 0.9985 | 0.9965 | 0.9807 | 41.19 | 0.8613 | 84.8902 |
| Allyl formate | 0.9997 | 0.9993 | 0.9963 | 1.99 | 0.6195 | 158.1618 |

Diagnostic of Model Adequacy

Figure 20:
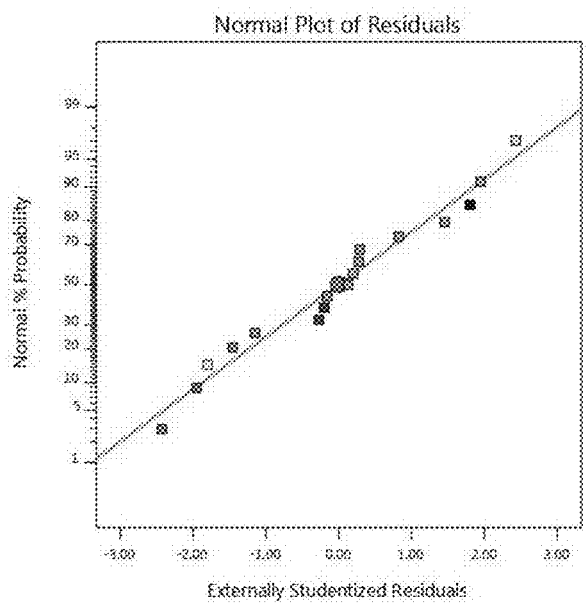
FIG. 20 depicts I—Normal plot of residuals of AA; II—Internally studentized residuals vs run for AA; III—Cook's distance for AA; IV—Cook's distance for AF.
Figure 20:
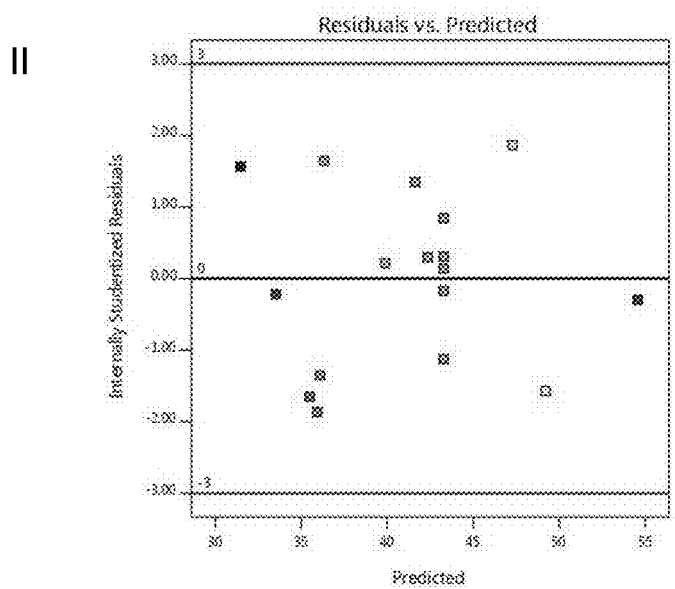
Figure 20:
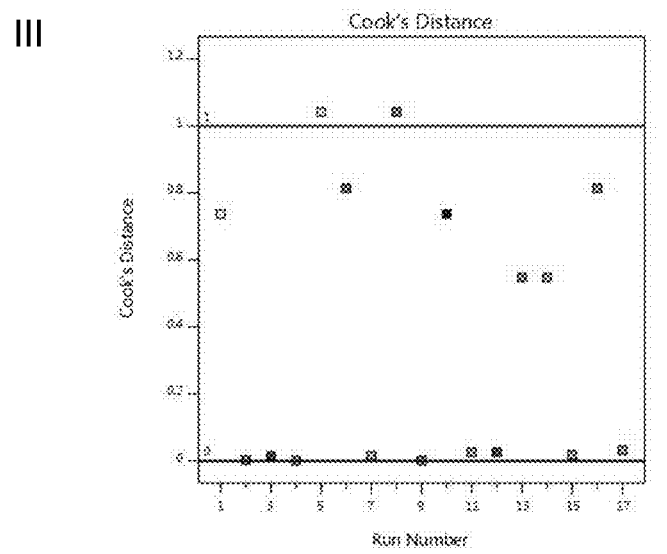
Figure 20:
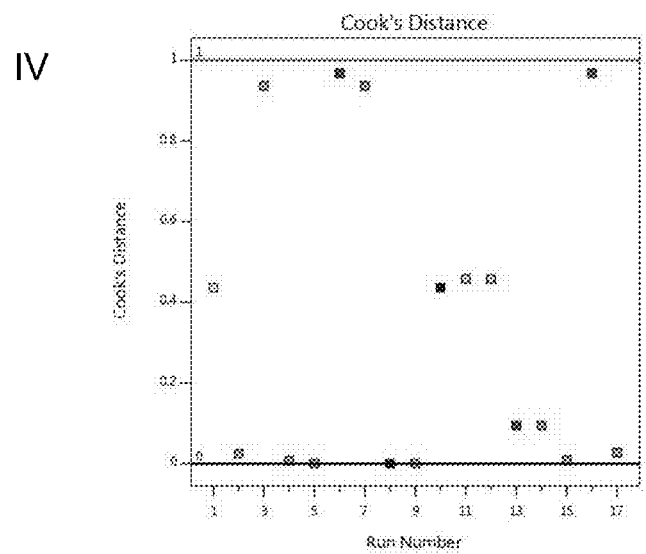

The obtained model underwent further analysis to diagnostic its validity. The normal % probability plot of residuals, the Box-Cox, the predicted versus actual values, the residual versus predicted values, the residual versus run values, the externally studentized residual versus factor plots, and Cook's distance plots were analyzed to estimate the adequacy of the models. The normal % probability versus the studentized residuals plot is linear indicating the normality of the residuals (FIG. 20-I) for AA and AF. FIG. 20-II shows a random distribution of the predicted values versus internally studentized residuals in order to get satisfactory model. The Cook's distance was checked for influential values (FIG. 20-III). There were two influential points out of the limits, run 5 and 8 for AA. In the case of AF, there were none points out of the limits, but four values were close to 1, indicating the high influence of the this points if they are remove from the model. The Box-Cox analysis indicates not transformation was required for the AA model. In the case of AF, indicates the best results for normality were reached with Lambda values between 0.46 and 0.85 after power transformation with the best value of Lambda equal to 0.66 (FIG. 20-IV)

Figure 21:
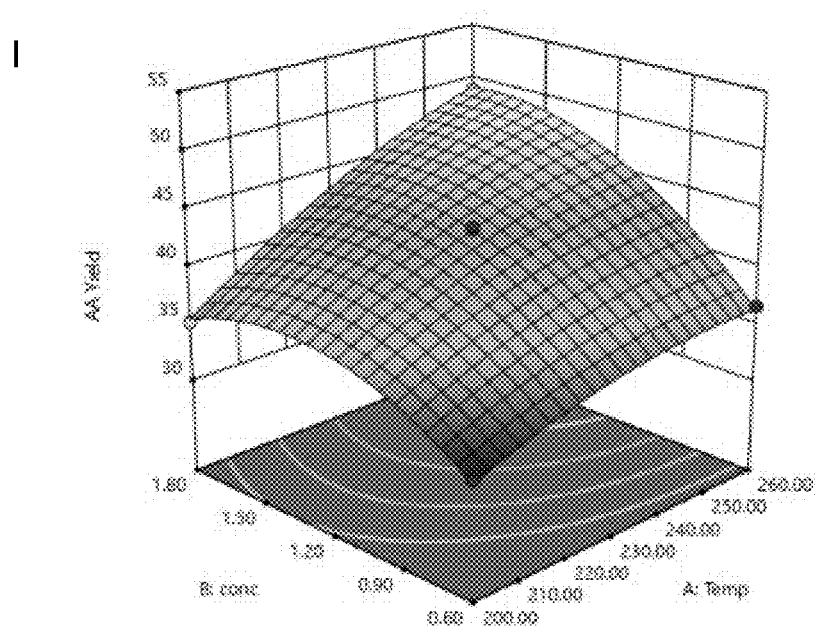
FIG. 21 depicts 3D surface plots for two-factors interaction for AAPY (I-III) and AFPY(IV-VI).
Figure 21:
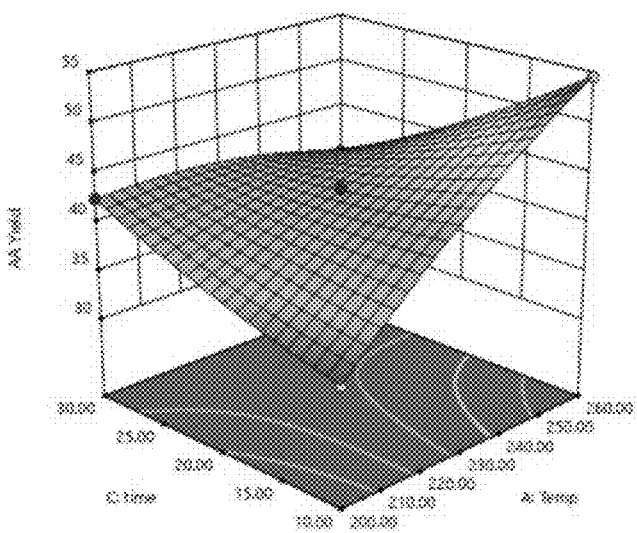
Figure 21:
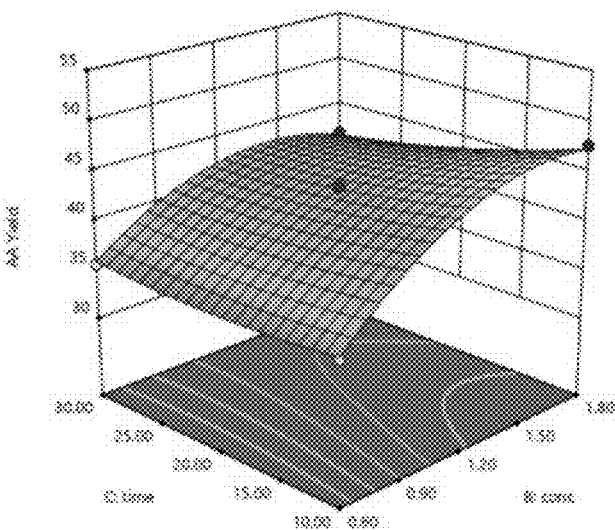
Figure 21:
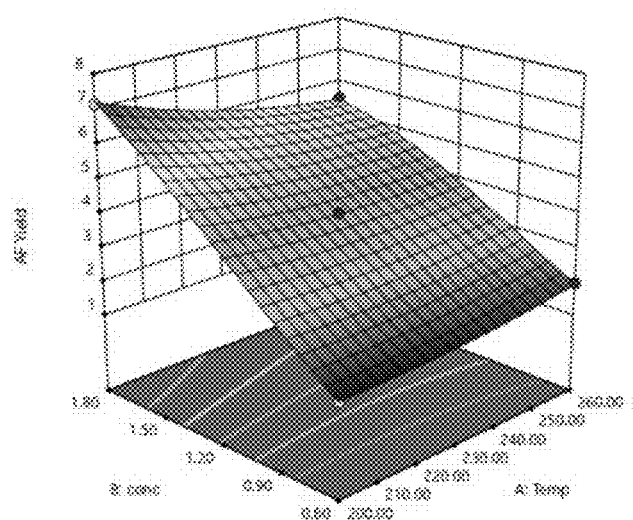
Figure 21:
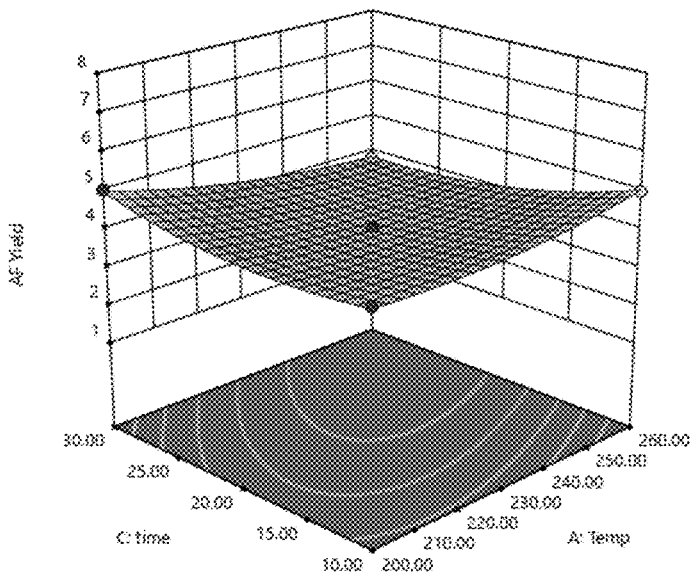
Figure 21:
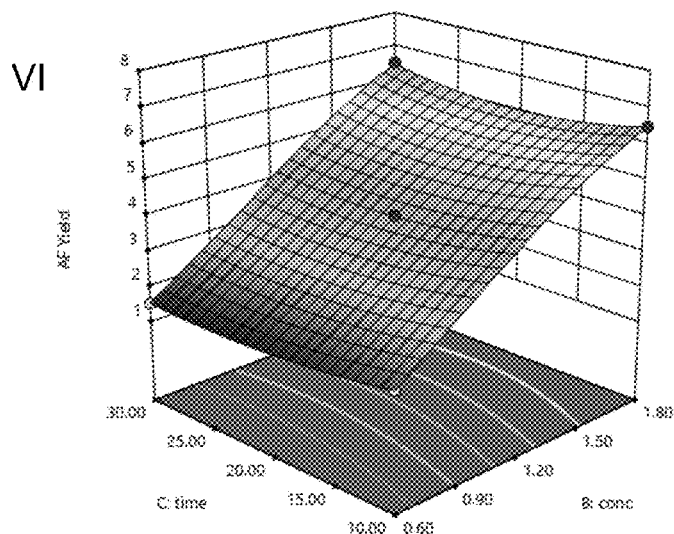

The FIG. 21 shows the 3D response surface plot for AA PY. FIG. 21-I shows the interactive effect of temperature and concentration in AA PY, where the interaction of both factors has an increase in the PY. FIG. 21-II shows the effect of time and temperature in AA PY. The temperature has a higher effect increasing the PY of AA, were the effect of the time is not significant. Comparing concentration and time interaction effect (FIG. 21-III), the concentration has a higher effect in the AA PY but it is negligible for the variable time. In general, temperature has a higher influence towards a higher yield of allyl alcohol; this is in agreement with other studies. As the temperature is increased, the DODH of glycerol is favorable to increased allyl alcohol yield. It is understandable that time doesn't have a big effect in the yield of allyl alcohol, as during experiments was noted that distillation stopped around 10 minutes of microwave irradiation after 260° C. temperature was reached, not making any difference in yield of allyl alcohol.

The 3D plots for allyl formate (FIG. 21-IV-VI) shows non-linear interactions too in correspondence with equation 3. In the formation of the by-product AF (FIG. 21-IV), the ratio Gly:FA has most higher influence than the temperature, which has almost a null influence. When analyzing between time and temperature, there is not much difference with this factor. But FIG. 21-VI confirms once more the high influence of the formation of AF when the ratio Gly:FA is increased. Therefore Gly:FA ratio has the higher influence among the two other factors. As allyl alcohol has an instantaneous reaction with formic acid towards allyl formate, as the concentration of formic acids is increased in the system, the probabilities of allyl formate increase leading to a reduction in allyl alcohol yield.

Optimization and Verification of the Model

The optimum conditions to increase the yield of AA were obtained using the Design Expert software applying the ramp method. The optimum conditions chosen were T=259.84° C., t=10.84 min, and Gly:FA ratio=1:1.57. Three set of experiments were performed in triplicate to confirm the model at three different levels with analysis in triplicate. The results are presented in Table 7.

TABLE 7

Results of experiments to confirm the validity of the model.

| Confirmation location | Response | Predicted Mean | Predicted Median* | Std Dev | SE Pred | 95% PI low | Data Mean† | 95% PI high |
|---|---|---|---|---|---|---|---|---|
| 1 | AA Yield | 57.0833 | 57.0833 | 0.35477 | 0.378691 | 56.1879 | 56.4333 | 57.9788 |
| | AF Yield‡ | 5.89264 | 5.89249 | 0.0599783 | N/A | 5.74207 | 5.74658 | 6.04485 |
| 2 | AA Yield | 54.7144 | 54.7144 | 0.35477 | 0.344998 | 53.8986 | 54.1667 | 55.5301 |
| | AF Yield‡ | 5.96852 | 5.96837 | 0.0603632 | N/A | 5.83037 | 5.86321 | 6.10798 |
| 3 | AA Yield | 49.0601 | 49.0601 | 0.35477 | 0.332956 | 48.2728 | 49.3767 | 49.8474 |
| | AF Yield‡ | 6.13486 | 6.1347 | 0.0611986 | N/A | 5.99964 | 6.09582 | 6.27127 |

†For transformed responses the data mean is calculated on the transformed scale.
‡Standard error (SE) not calculated on original scale.

Effect of the Model Terms on the AA PY

The surface area plots were built with chosen models to better understand the main and interactive effects of the independent variables in the AA PY and AF PY. The 3D response surface plots for AA and AF are presented in FIG. 21. The plots were prepared by keeping one variable constant and changing the other two variables within the study range. As FIG. 21 shows the relationship among the variables is non-linear in agreement with the quadratic equation (2). This is the same case for the AF PY, were all the plots are non-linear.

Microwave-Assisted Allyl Alcohol Conversion to Diallyl Phthalate

Allyl alcohol and phthalic anhydride were reacted under microwave using sulfuric acid as catalyst. Using quick TLC test, two new compounds were found in the raw mixture. In order to identify the products, a column separation was performed.

Figure 22:
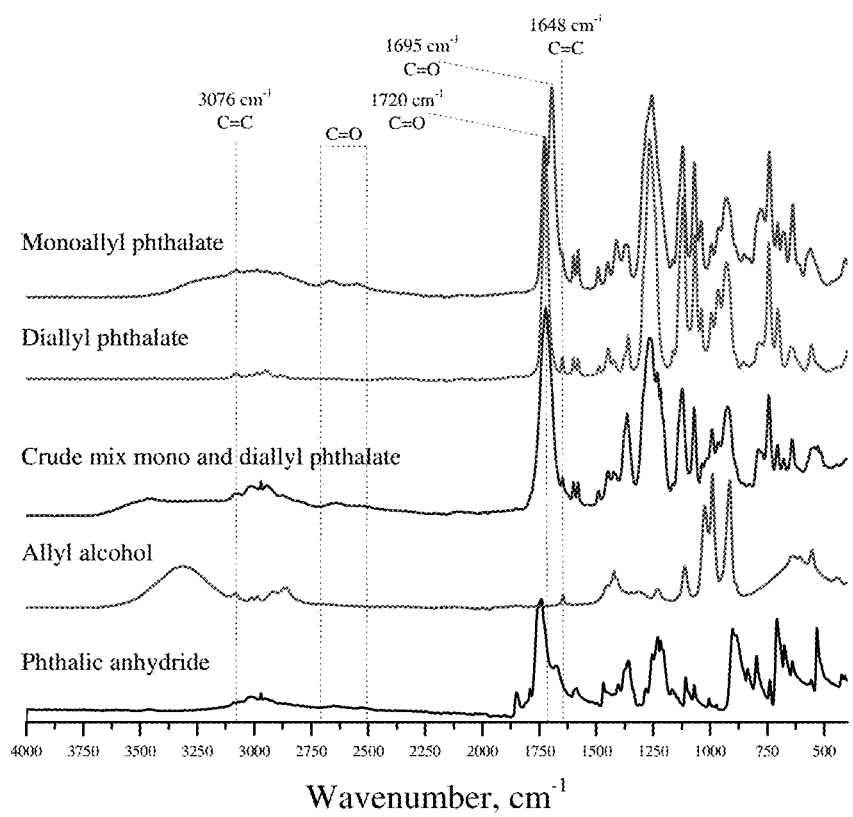
FIG. 22 depicts ATR FT IR of reagents and products of the phthalic and allyl alcohol.

The crude mixture of the reaction, monoallyl, and diallyl phthalate were characterized using ATR-FT IR (FIG. 22). The allyl bands corresponding to C=C stretching are identified at 3076 and 1648 $cm^{-1}$ for the mono- and diallyl alcohol. For the monoallyl alcohol, the carbonyl (C=O) broad peaks of carboxylic acid are observed at 2500-2700 cm$^{-1}$ and 2700-3300 cm$^{-1}$. Additionally, the carbonyl peak of carboxylic acid shows at 1695 cm$^{-1}$ as a split peak with the carbonyl peak attached to the allyl group at 1720 cm$^{-1}$.

Figure 23:
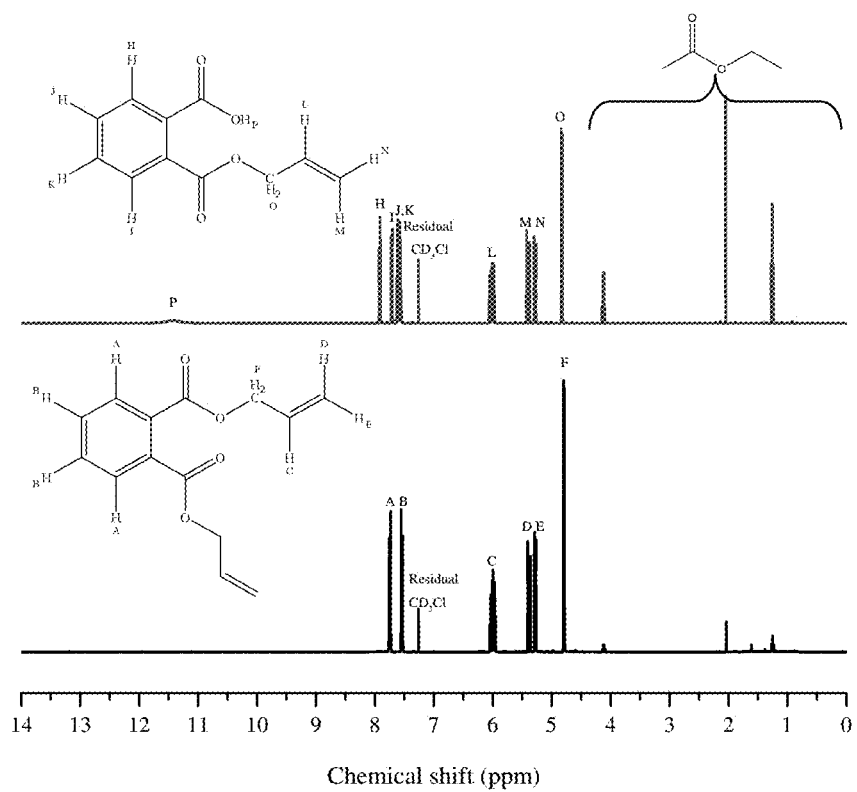
FIG. 23 depicts $^1$H-NMR spectra of diallyl phthalate and monoallyl phthalate in CD$_3$Cl after column purification.

$^1$-H NMR spectra of monoallyl and diallyl phthalate were conducted to confirm their chemical structures. Two peaks (7.54 and 7.75) are associated to the benzene ring in the diallyl phthalate and three are associated to the monoallyl alcohol (7.59, 7.71, 7.92). The allyl protons "C" and "L" both placed at 6 ppm corresponded to diallyl and mono respectively, as the integration indicates two protons for "C" and one for "L". Some residues of ethyl acetate were identified as impurities from the separation process. (FIG. 23).

Microwave-Assisted Synthesis of Poly(Diallyl Phthalate).

Figure 24:
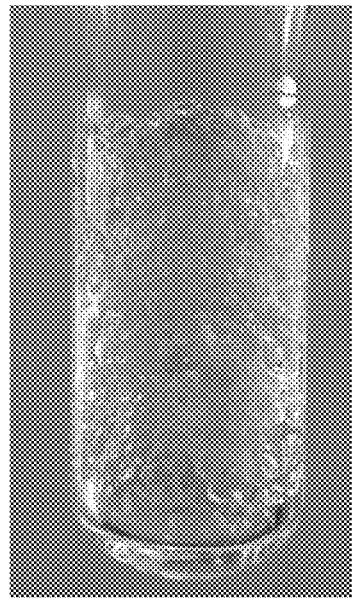
FIG. 24 depicts 1-Raw poly (diallyl phthalate) after microwave polymerization of diallyl phthalate in the presence of benzoyl peroxide II-poly (diallyl phthalate) after washing with methanol and dried at 80° C.
Figure 24:
Figure 25:
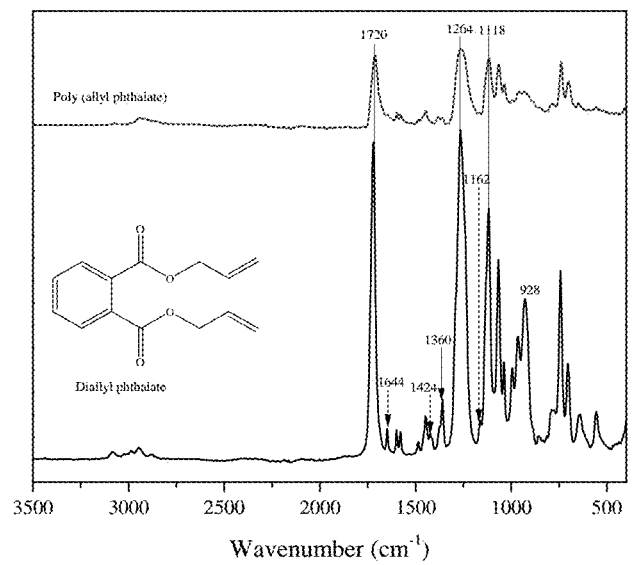
FIG. 25 depicts ATR-FT IR of diallyl phthalate and poly (diallyl phthalate) after MW polymerization.
Figure 26:
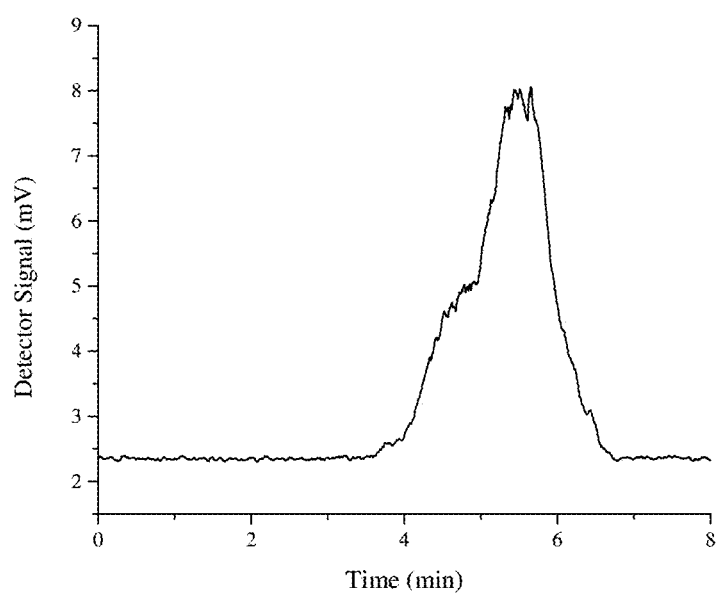
FIG. 26 depicts GPC of poly (diallyl phthalate) in THF.

The polymerization of diallyl phthalate using the microwave was confirmed by the appearance of a white-yellow solid after microwave reaction as seen in FIG. 24. The product was characterized by ATR-FT IR (FIG. 25). The phthalate group more notable bands are located at 1720, 1264, and 1118 cm$^{-1}$ and are associated to the C=O and C—O—C stretching vibrations$^1$. These bands are also the predominant ones in the polymer. After polymerization the bands located at 1644, 1424, 1360, and 935 cm$^{-1}$ are reduced in intensity. Among the latest set of bands, the one at 1644 cm$^{-1}$ is due to the C=C stretching vibration in the allyl portion of the diallyl phthalate molecule and it is considerably reduced after the polymerization. The molecular weight of the polymer was identified with GPC. The results are shown in FIG. 26. The shape of the plot shows a wide peak with a shoulder peak. A value of polydispersity of 6.62 indicates a material with a high polydispersity, compose for more than one polymer length.

Figure 27:
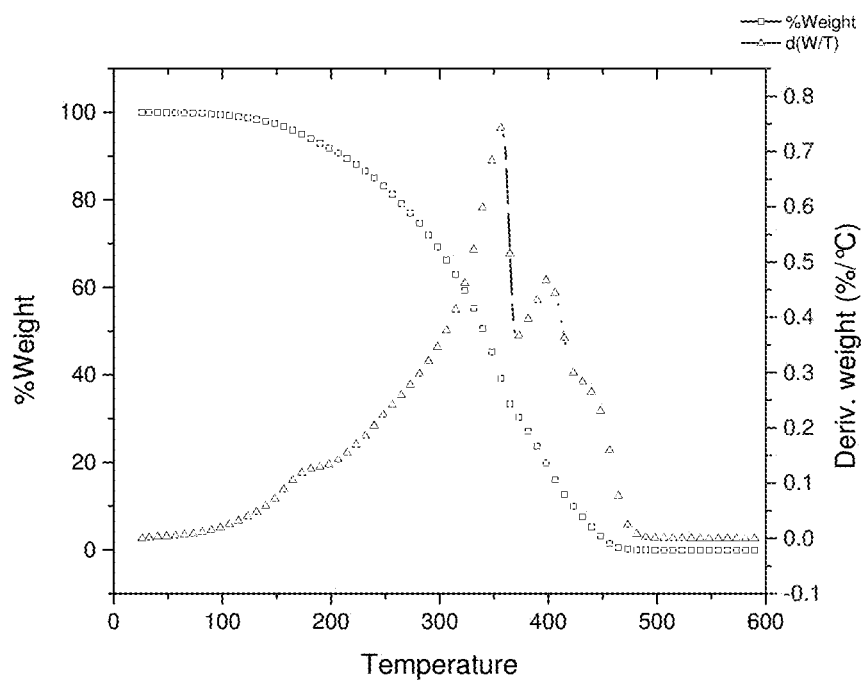
FIG. 27 depicts TGA/DTGA of poly (diallyl phthalate).

The initial degradation, T$_{d,5\ wt\ \%}$ happens at 273.12° C., the half lost degradation occurs at 383° C. with a residual weight of 2.6% at 600° C. (FIG. 27)

Figure 28:
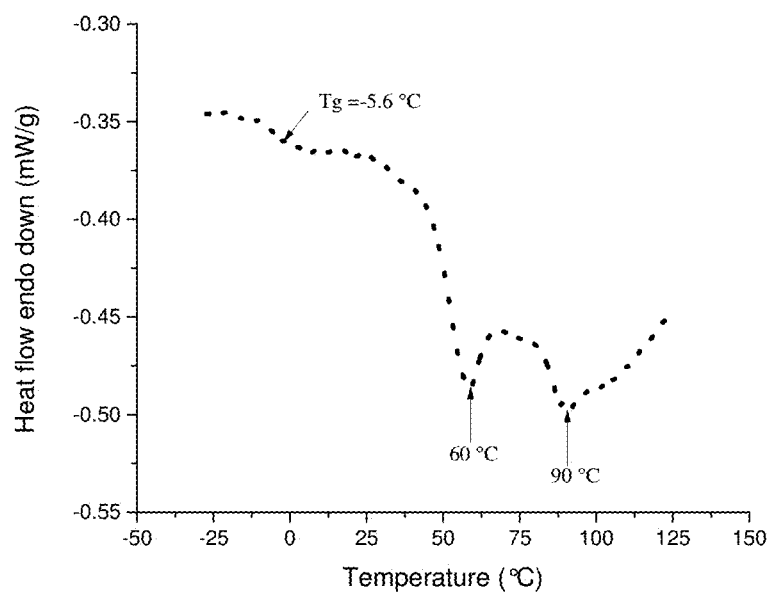
FIG. 28 depicts DSC thermograms of poly (diallyl phthalate).

The DSC curve of polly (diallyl phthalate) is shown in FIG. 28, which shows the Tg at −5.6° C. There are two endothermic peaks at 60 and 90° C. which correspond to the melting points of the polymers. These two peaks are in agreement with the high polydispersity of the polymers, as shown in FIG. 26.

Figure 29:
FIG. 29 depicts the consolidation and dewatering image of MFT after treatment with PAM and developed biopolymers PAA and PAF
Figure 30:
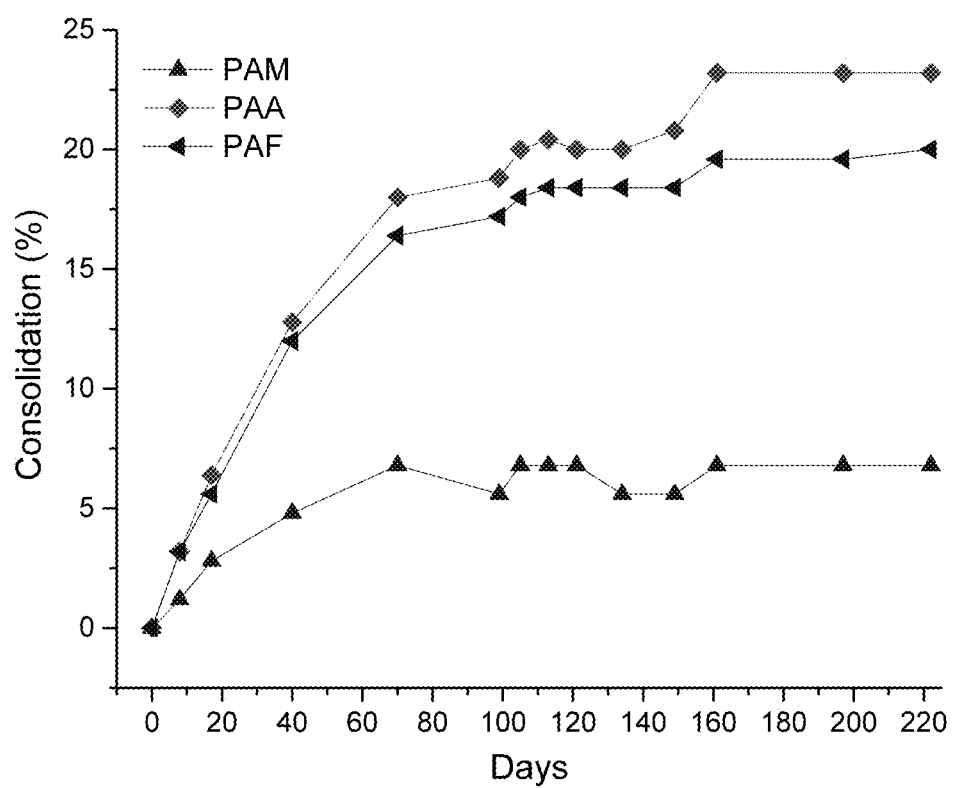
FIG. 30 depicts the consolidation (%) of mature fine tailings (250 mL) after treating with 200 ppm conc. of PAM, PAA and PAF.
Figure 31:
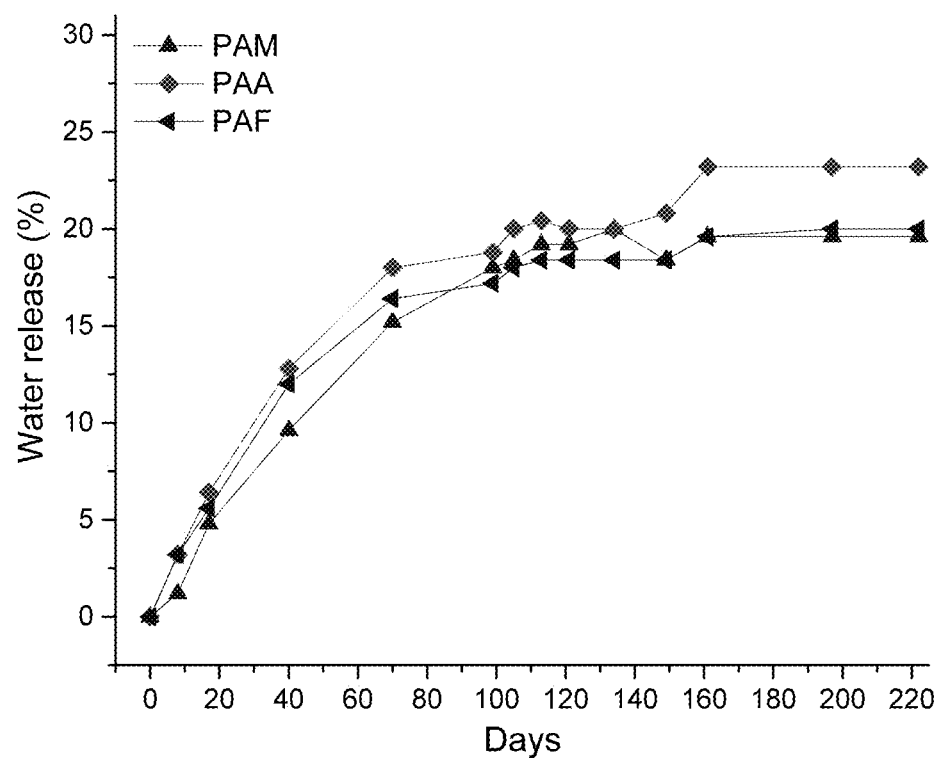
FIG. 31 depicts the water release (%) of mature fine tailings (250 mL) after treating with 200 ppm conc. of PAM, PAA and PAF.

Testing of Polyallyl Alcohol (PAA) and Polyallyl Formate (PAF) in Consolidation of Oil Sands Tailings The developed biopolymers PAA and PAF were tested to consolidate MFT and compared with commercial synthetic polymer PAM. The Mature fine tailings (MFT) from oil sand industry were treated with developed biopolymers for dewatering and consolidation. For this purpose, 50 mg (200 ppm) of flocculants poly(acrylamide) (PAM), poly(allyl alcohol) (PAA) and poly(allyl formate) (PAF) were individually added into 250 mL volume of tailings and stirred for five minutes and then let to settle. All the treated fractions were added into a 250 mL glass column, which were analysed frequently to observe/measure the consolidation and dewatering rate of MFT (FIGS. 29, 30 & 31, table 8 & 9). Over a period of 220 days, the synthesized biopolymers PAA and PAF exhibited about 20-25% consolidation compared to about 7% consolidation in tailings treated with PAM and almost comparable or slightly better water recovery. This innovative technology not only uses abundant waste material generated by biofuel industry but could also solves a huge issue of tailing consolidation.

TABLE 8

Consolidation (%) of MFT on treatment with different flocculants.

| Samples | 0 days | 8 days | 17 days | 40 days | 70 days | 99 days | 105 days | 113 days | 121 days | 134 days | 149 days | 161 days | 197 days | 222 days |
|---|---|---|---|---|---|---|---|---|---|---|---|---|---|---|
| PAM | 0 | 1.2 | 2.8 | 4.8 | 6.8 | 5.6 | 6.8 | 6.8 | 6.8 | 5.6 | 5.6 | 6.8 | 6.8 | 6.8 |
| PAA | 0 | 3.2 | 6.4 | 12.8 | 18 | 18.8 | 20 | 20.4 | 20 | 20 | 20.8 | 23.2 | 23.2 | 23.2 |
| PAF | 0 | 3.2 | 5.6 | 12 | 16.4 | 17.2 | 18 | 18.4 | 18.4 | 18.4 | 18.4 | 19.6 | 19.6 | 20 |

TABLE 9

Water released by MFT on treatment with different flocculants.

| Samples | 0 days | 8 days | 17 days | 40 days | 70 days | 99 days | 105 days | 113 days | 121 days | 134 days | 149 days | 161 days | 197 days | 222 days |
|---|---|---|---|---|---|---|---|---|---|---|---|---|---|---|
| PAM | 0 | 1.2 | 4.8 | 9.6 | 15.2 | 18 | 18.4 | 19.2 | 19.2 | 20 | 18.4 | 19.6 | 19.6 | 19.6 |
| PAA | 0 | 3.2 | 6.4 | 12.8 | 18 | 18.8 | 20 | 20.4 | 20 | 20 | 20.8 | 23.2 | 23.2 | 23.2 |
| PAF | 0 | 3.2 | 5.6 | 12 | 16.4 | 17.2 | 18 | 18.4 | 18.4 | 18.4 | 18.4 | 19.6 | 20 | 20 |

The embodiments described herein are intended to be examples only. Alterations, modifications and variations can be effected to the particular embodiments by those of skill in the art. The scope of the claims should not be limited by the particular embodiments set forth herein, but should be construed in a manner consistent with the specification as a whole.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A method of converting glycerol to an allyl compound, comprising:
   a) deoxydehydrating glycerol with formic acid and heat to form allyl alcohol; and b) esterifying the allyl alcohol with formic acid and heat to form allyl formate.

2. The method of claim 1, wherein the heat of step a) and step b) is generated by a microwave.

3. The method of claim 2, wherein the allyl alcohol is step a) is formed by distillation and the allyl formate in step b) is formed by reflux.

4. The method of claim 1, wherein deoxydehydrating the glycerol with the formic acid and heat to form the allyl alcohol comprises heating the glycerol and the formic acid to 195° C., and then heating the glycerol and the formic acid to 240° C.

5. The method of claim 4, further comprising isolating the allyl alcohol while heating the glycerol and the formic acid to 240° C.

6. The method of claim 5, further comprising cooling the glycerol and the formic acid to between 95°-100° C., and then adding more of the formic acid.

7. The method of claim 5, wherein esterifying the allyl alcohol with formic acid and heat to form allyl formate comprises heating the allyl alcohol and formic acid at 60° C.

8. The method of claim 5, wherein the allyl alcohol formed has a purity of ≥90%.

9. The method of claim 5, wherein the allyl formate formed has a purity of ≥85%.

10. The method of claim 6, further comprising polymerizing the allyl formate using α,α'-azoisobutyronitrile, tert-butyl perbenzoate, di-tert-butyl peroxide, tert-butyl hydroperoxide, or benzoyl peroxide and heat to form poly(allyl formate).

11. The method of claim 10, wherein the poly(allyl formate) has a molecular weight of at least 1000 g/mol.

12. A method of converting glycerol to an allyl polymer, comprising:
a) deoxydehydrating glycerol with formic acid and heat to form allyl alcohol; and
b) polymerizing the allyl alcohol using a radical initiator and heat to form poly(allyl alcohol);
wherein the heat of step (a) and step (b) is generated by a microwave.

13. The method of claim 12, wherein the allyl alcohol is step a) is formed by distillation and the poly(allyl alcohol) in step b) is formed by reflux.

14. The method of claim 12, wherein deoxydehydrating the glycerol with the formic acid and heat to form the allyl alcohol comprises heating the glycerol and the formic acid to 195° C., and then heating the glycerol and the formic acid to 260° C.

15. The method of claim 12, further comprising isolating the allyl alcohol while heating the glycerol and the formic acid to 260° C.

16. The method of claim 15, further comprising cooling the glycerol and the formic acid to between 95°-100° C., and then adding more of the formic acid.

17. The method of claim 16, wherein the allyl alcohol formed has a purity of ≥90%.

18. The method of claim 16, wherein the allyl alcohol formed has a purity of 95%.

19. The method of claim 16, wherein the poly(allyl alcohol) has a molecular weight of at least 2400 g/mol.

* * * * *